(12) United States Patent
Usmani et al.

(10) Patent No.: US 10,656,144 B2
(45) Date of Patent: May 19, 2020

(54) IMMUNE PROFILING AND MINIMAL RESIDUE DISEASE FOLLOWING STEM CELL TRANSPLANTATION IN MULTIPLE MYELOMA

(71) Applicant: The Charlotte Mecklenburg Hospital Authority, Charlotte, NC (US)

(72) Inventors: Saad Z. Usmani, Charlotte, NC (US); Manisha Bhutani, Charlotte, NC (US); Qing Zhang, Charlotte, NC (US); David M. Foureau, Matthews, NC (US)

(73) Assignee: The Charlotte Mecklenburg Hospital Authority, Charlotte, NC (US)

( * ) Notice: Subject to any disclaimer, the term of this patent is extended or adjusted under 35 U.S.C. 154(b) by 0 days.

(21) Appl. No.: 15/829,611

(22) Filed: Dec. 1, 2017

(65) Prior Publication Data
US 2018/0156784 A1   Jun. 7, 2018

Related U.S. Application Data

(60) Provisional application No. 62/577,197, filed on Oct. 26, 2017, provisional application No. 62/429,269, filed on Dec. 2, 2016.

(51) Int. Cl.
| | | |
|---|---|---|
| *G01N 33/50* | (2006.01) | |
| *G01N 33/68* | (2006.01) | |
| *G01N 33/574* | (2006.01) | |
| *G01N 33/74* | (2006.01) | |

(52) U.S. Cl.
CPC ... *G01N 33/5091* (2013.01); *G01N 33/57407* (2013.01); *G01N 33/57426* (2013.01); *G01N 33/6869* (2013.01); *G01N 33/74* (2013.01); *G01N 2333/475* (2013.01); *G01N 2333/49* (2013.01); *G01N 2333/50* (2013.01); *G01N 2333/5434* (2013.01); *G01N 2800/245* (2013.01)

(58) Field of Classification Search
CPC ............ G01N 33/6869; G01N 33/74
See application file for complete search history.

(56) References Cited

PUBLICATIONS

Sarkar et al., (Cancer Immunol Immunother. 2015;64:951-963) (Year: 2015).*
Costello et al. (Immunology Jul. 2013;139(3):338-41) (Year: 2013).*
Foley et al., (Immunol Rev. Mar. 2014;258(1):45-63) (Year: 2014).*
Leung et al., (Clin Cancer Res Jul. 1, 2014;20(13):3390-3400) (Year: 2014).*
Navarro et al., (J Immunol. Dec. 15, 2014; 193(12): 6192-6206) (Year: 2014).*
Koehl et al., (Oncoimmunology. Nov. 11, 2015;5(4):e1115178. eCollection Apr. 2016) (Year: 2015).*
Waiker et al (J Am Soc Nephrol. Jan. 2012; 23(1):13-21) (Year: 2012).*
Brooks (Genome Res. Feb. 2012;22(2):183-7) (Year: 2012).*
Bai et al (Br J Haematol. Apr. 2018;181(1):11-26) (Year: 2018).*
Foureau et al (Blood 2016 128:378; published online Dec. 1, 2016) (Year: 2016).*
Bhutani et al. "Investigation of a gene signature to predict response to immunomodulatory derivatives for patients with multiple myeloma: an exploratory, retrospective study using microarray datasets from prospective clinical trials" *The Lancet, Haematology* 4:e443-e451 (2017).
Burington et al. "Tumor Cell Gene Expression Changes Following Short-term In vivo Exposure to Single Agent Chemotherapeutics are Related to Survival in Multiple Myeloma" *Clinical Cancer Research* 14(15):4821-4829 (2008).
Decaux et al. "Prediction of Survival in Multiple Myeloma Based on Gene Expression Profiles Reveals Cell Cycle and Chromosomal Instability Signatures in High-Risk Patients and Hyperdiploid Signatures in Low-Risk Patients: A Study of the Intergroupe Francophone du Myélome" *Journal of Clinical Oncology* 26(29):4798-4805 (2008).
Foureau et al. "Peripheral Immune Profile and Minimal Residual Disease (MRD) Burden Following Autologous Stem Cell Transplantation (ASCT) in Multiple Myeloma (MM)" *Blood* 128(22):378 (Abstract available online Nov. 2016).
Heuck et al. "Five gene probes carry most of the discriminatory power of the 70-gene risk model in multiple myeloma" *Leukemia* 28:2410-2413 (2014).
Krönke et al. "IKZF1 expression is a prognostic marker in newly diagnosed standard-risk multiple myeloma treated with lenalidomide and intensive chemotherapy: a study of the German Myeloma Study Group (DSMM)" *Leukemia* 31(6):1363-1367 (2017) (Abstract only).
Kuiper et al. "A gene expression signature for high-risk multiple myeloma" *Leukemia* 26:2406-2413 (2012).
Nair et al. "Superior results of Total Therapy 3 (2003-33) in gene expression profiling-defined low-risk multiple myeloma confirmed in subsequent trial 2006-66 with VRD maintenance" *Blood* 115(21):4168-4173 (2010).
Pan et al. "NFAT Gene Family in Inflammation and Cancer" *Current Molecular Medicine* 13(4):543-554 (2013).

(Continued)

*Primary Examiner* — Brian Gangle
*Assistant Examiner* — Andrea K McCollum
(74) *Attorney, Agent, or Firm* — Myers Bigel, P.A.

(57) ABSTRACT

The present invention provides methods for determining the level or status of minimal residue disease (MRD) in a multiple myeloma (MM) patient including analyzing peripheral natural killer (NK), NK-T and T cell distribution and/or activation, and quantifying inflammatory cytokines, chemokines and growth factors in a biological sample obtained from an MM patient to provide a peripheral immune profile; and obtaining a level or status of MRD in the MM patient from the peripheral immune profile, wherein if the peripheral immune profile exceeds a pre-determined threshold, the MM patient is positive for MRD.

7 Claims, 14 Drawing Sheets

(56) References Cited

PUBLICATIONS

Shaughnessy et al. "A validated gene expression model of high-risk multiple myeloma is defined by deregulated expression of genes mapping to chromosome 1" *Blood* 109:2276-2284 (2007).

Shaughnessy et al. "Pharmacogenomics of bortezomib test-dosing identifies hyperexpression of proteasome genes, especially PSMD4, as novel high-risk feature in myeloma treated with Total Therapy 3" *Blood* 118(13):3512-3524 (2011).

Zhou et al. "Prediction of cytogenetic abnormalities with gene expression profiles" *Blood* 119(21):e148-e150 (2012).

\* cited by examiner

IMMUNE PROFILING AND MINIMAL RESIDUE DISEASE FOLLOWING STEM CELL TRANSPLANTATION IN MULTIPLE MYELOMA

STATEMENT OF PRIORITY

This application claims the benefit, under 35 U.S.C. § 119(e), of U.S. Provisional Application Ser. No. 62/429,269, filed Dec. 2, 2016, and U.S. Provisional Application Ser. No. 62/62/577,197, filed Oct. 26, 2017, the entire contents of each of which are incorporated by reference herein.

RESERVATION OF COPYRIGHT

A portion of the disclosure of this patent document contains material which is subject to copyright protection. The copyright owner, The Charlotte-Mecklenburg Hospital Authority, doing business as "Carolinas HealthCare System," Charlotte, N.C., has no objection to the reproduction by anyone of the patent document or the patent disclosure, as it appears in the U.S. Patent and Trademark Office patent file or records, but otherwise reserves all copyright rights whatsoever.

FIELD OF THE INVENTION

The present invention relates to use of a peripheral immune profile in the assessment of minimal residue disease (MRD) burden in multiple myeloma (MM) patients following autologous stem cell transplantation (ASCT).

BACKGROUND OF THE INVENTION

The immune system plays an essential role in both promoting and inhibiting the growth of multiple myeloma. Loss of anti-myeloma immunity involves compromised activation and expansion of myeloma-specific T and NK cells, and an immunologic milieu that fosters disease progression. The immune suppressive phenotype of MM can be targeted and reversed (partially or completely) in responding patients, suggesting that anti-myeloma treatment has the potential to activate immune responses. Increasingly, evidence has shown strong association between deepest level of clinical response, represented by an MRD negative status, and favorable survival outcome after autologous stem cell transplantation (ASCT). It was reasoned that immune profiling pattern post-ASCT correlates with depth of response, the immune profile of $MRD^{pos}$ patients is distinct from $MRD^{neg}$ patients and thus, analysis of the immune profile for MM patients can be used as this predictor following ASCT treatment of MM.

SUMMARY OF THE INVENTION

The present invention relates to use of a peripheral immune profile as a predictor for MRD burden in MM patients.

Thus, according to an aspect of the invention, provided in a method for determining the extent of minimal residue disease (MRD) in a multiple myeloma (MM) patient comprising: obtaining a biological sample from an MM patient; analyzing peripheral NK, NK-T and T cell distribution and/or activation, and quantifying inflammatory cytokines, chemokines and growth factors in the biological sample to provide a peripheral immune profile; and obtaining an MRD status from the immune variable profile, wherein if the peripheral immune profile exceeds a pre-determined threshold, the MM patient is positive for MRD.

According to another aspect of the invention, provided is a method of determining or assessing efficacy of treatment of an MM patient comprising: obtaining a biological sample from the MM patient; analyzing peripheral NK, NK-T and T cell distribution and/or activation, and quantifying inflammatory cytokines, chemokines and growth factors in the biological sample to provide a peripheral immune profile; and obtaining a level or status of MRD in the MM patient from the peripheral immune profile, wherein if the peripheral immune profile does not exceed a pre-determined threshold, the MM patient is negative for MRD.

According to another aspect of the invention, provided is a method of determining or assessing MRD in an MM patient comprising: obtaining a biological sample from the MM patient; analyzing peripheral NK, NK-T and T cell distribution and/or activation, and quantifying inflammatory cytokines, chemokines and growth factors in the biological sample to provide a peripheral immune profile; and obtaining a level or status of MRD in the MM patient from the peripheral immune profile, wherein if the peripheral immune profile does not exceed a pre-determined threshold, the MM patient is negative for MRD.

DETAILED DESCRIPTION OF THE INVENTION

Figure 1:
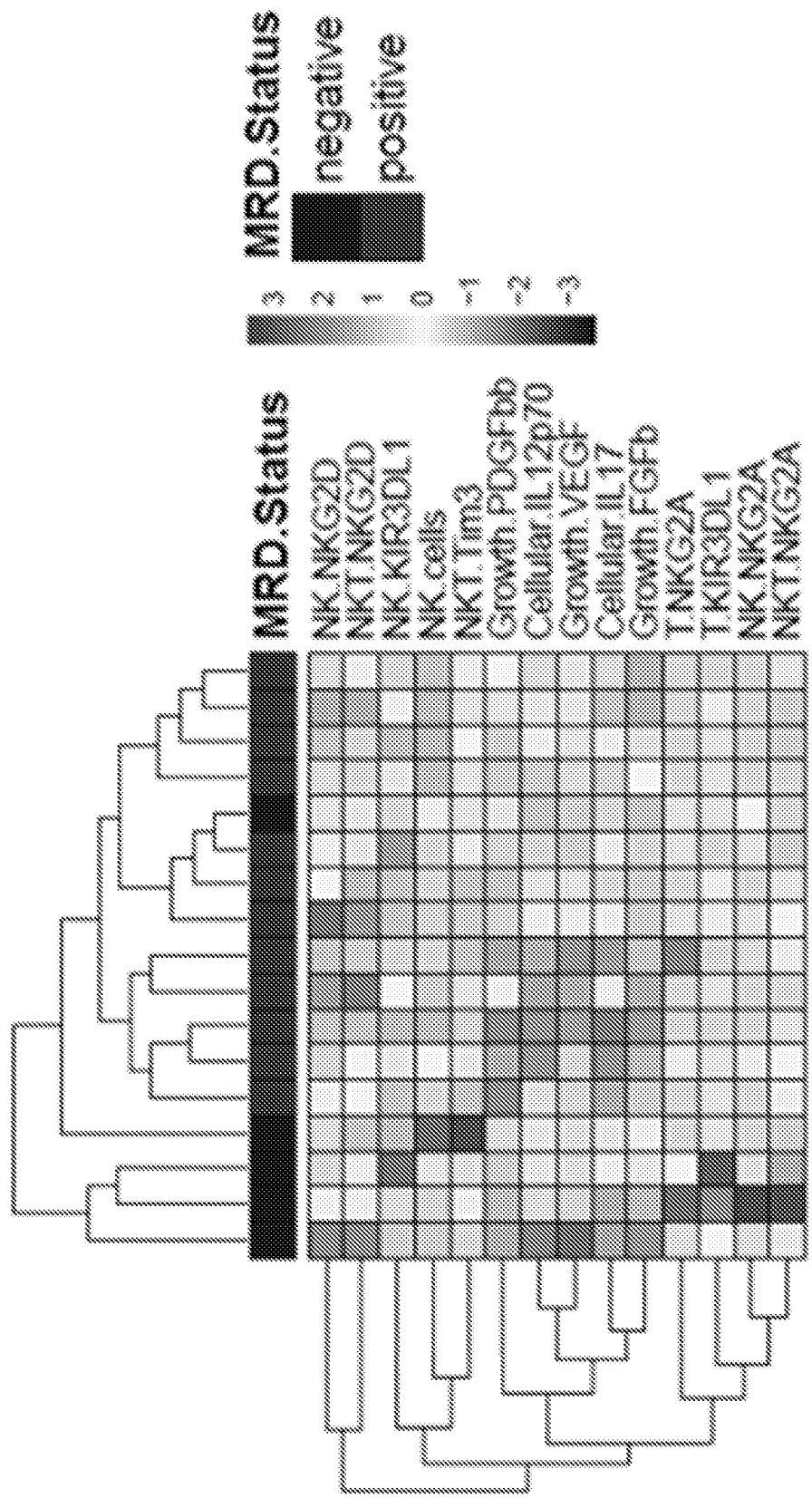
FIG. 1 depicts an expression profile heat map of selected peripheral immune markers differentiating $MRD^{neg}$ and $MRD^{pos}$ patients post-ASCT.

The present invention is more particularly described in the following examples that are intended as illustrative only since numerous modifications and variations therein will be apparent to those skilled in the art.

Articles "a" and "an" are used herein to refer to one or to more than one (i.e., at least one) of the grammatical object of the article. By way of example, "an element" means at least one element and can include more than one element.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

"Multiple myeloma" or "MM" refers to a cancer of plasma cells in the bone marrow. Uncontrolled growth of these plasma cells can lead to bone pain and fractures, anemia, infections, kidney failure and other complications. Risk factors for MM include drinking alcohol and obesity. Although treatable, remission may occur with treatment with steroids, chemotherapy and/or stem cell transplant.

"Minimal residual disease" (MRD) or "measureable residual disease" represent residual malignant cells that remain in the patient during treatment, or after treatment when the patient is in remission, for example subclinical levels of residual leukemia during treatment, or after the patient has entered remission.

The term "sample" as used herein relates to a material or mixture of materials, typically, although not necessarily, in fluid form, containing one or more components of interest.

The term "biological sample" includes any sample, or portion thereof, that may be taken from a subject that contains genetic material that can be used in the methods provided herein. For example, a biological sample may include a sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Particular biological samples include, but are not limited to, whole blood, partially purified blood, PBMCs, tissue biopsies, and the like. In some embodiments, the biological sample is a bone marrow, urine and/or blood sample. In some embodiments, the sample may comprise plasma cells obtained from bone marrow, urine and/or blood.

"Patient" or "subject" is used interchangeably. A patient or subject of this invention is any patient or subject with a cancer such as MM. In some embodiments, the subject is a human; however, a subject of this invention can include an animal subject, particularly mammalian subjects such as canines, felines, bovines, caprines, equines, ovines, porcines, rodents (e.g. rats and mice), lagomorphs, primates (including non-human primates), etc., including domesticated animals, companion animals and wild animals for veterinary medicine or treatment or pharmaceutical drug development purposes. The subjects relevant to this invention may be male or female and may be any species and of any race or ethnicity, including, but not limited to, Caucasian, African-American, African, Asian, Hispanic, Indian, etc., and combined backgrounds. The subjects may be of any age, including newborn, neonate, infant, child, adolescent, adult, and geriatric and male or female. In some embodiments of the invention, the subject is a newly diagnosed and untreated patient, a newly diagnosed patient undergoing treatment, or a relapsed patient undergoing salvage treatments or salvage transplants.

In one aspect the present invention provides a method for determining the level or status of minimal residue disease (MRD) in a multiple myeloma (MM) patient comprising: analyzing peripheral NK, NK-T and T cell distribution and/or activation, and quantifying inflammatory cytokines, chemokines and growth factors in a biological sample obtained from an MM patient to provide a peripheral immune profile; and obtaining a level or status of MRD in the MM patient from the peripheral immune profile, wherein if the peripheral immune profile exceeds a pre-determined threshold, the MM patient is positive for MRD and if the peripheral immune profile does not exceed a pre-determined threshold, the MM patient is negative for MRD.

In a further aspect, the present invention provides a method of determining or assessing efficacy of treatment of an MM patient comprising: obtaining a biological sample from the MM patient that has received and/or is receiving treatment for MM and/or will undergo treatment; analyzing peripheral NK, NK-T and T cell distribution and/or activation, and quantifying inflammatory cytokines, chemokines and growth factors in a biological sample obtained from an MM patient to provide a peripheral immune profile; and obtaining a level or status of MRD in the MM patient from the peripheral immune profile, wherein if the peripheral immune profile exceeds a pre-determined threshold, the MM patient is positive for MRD and if the peripheral immune profile does not exceed a pre-determined threshold, the MM patient is negative for MRD.

In an additional aspect, the present invention provides a method of determining or assessing MRD in an MM patient comprising: analyzing peripheral NK, NK-T and T cell distribution and/or activation, and quantifying inflammatory cytokines, chemokines and growth factors in a biological sample obtained from an MM patient to provide a peripheral immune profile; and obtaining a level or status of MRD in the MM patient from the peripheral immune profile, wherein if the peripheral immune profile exceeds a pre-determined threshold, the MM patient is positive for MRD and if the peripheral immune profile does not exceed a pre-determined threshold, the MM patient is negative for MRD.

In the methods of this invention, the MM patient or subject can be a newly diagnosed and untreated patient, a newly diagnosed patient undergoing or having undergone treatment, or a relapsed patient undergoing salvage treatments or salvage transplants.

In the methods of this invention, the level or status of MRD in the MM patient can be determined following autologous stem cell transplantation (ASCT).

In the methods of this invention, the analyzing of peripheral NK, NK-T and T cell distribution and/or activation can comprise, consist essentially of, and/or consist of analyzing NK cell distribution, and analyzing NKG2D expression in NK and NK-T cells, KIR3DL1 expression in NK and T cells, NKG2A expression in NK, NK-T and T cells, and Tim3 expression in NK-T cells.

In the methods of this invention, the quantifying of inflammatory cytokines, chemokines and/or growth factors can comprise, consist essentially of, and/or consist of quantifying IL-12p70 and IL-12 pro-inflammatory cytokines, and/or quantifying FGF, PDGF and VEGF pro-angiogenic growth factors.

The methods of this invention can further comprise the step of initiating, reinstating, increasing and/or maintaining treatment of the MM patient that is positive for MRD and reducing, tapering off and/or discontinuing treatment of the MM patient that is negative for MRD.

A treatment of this invention can include steroids, chemotherapy, stem cell transplantation, autologous stem cell transplantation (ASCT), induction therapy, immunomodulatory drug (IMiD) therapy, thalidomide treatment, lenalidomide treatment, pomalidomide treatment, proteasome inhibitor treatment, non-IMiD therapy, any other treatment for multiple myeloma (MM), singly or in any combination and effective dosage.

As used herein, a "non-IMiD therapy" is a therapy that does not include an IMiD. For example, the therapy can exclude any of thalidomide, lenalidomide and pomalidomide, derivatives thereof and analogs thereof, as well as any other agent identified as an IMiD, in any combination, or all together. Thus, in some embodiments, the therapy can include one or more of thalidomide, lenalidomide and pomalidomide, derivatives thereof and analogs thereof, as well as any other agent identified as an IMiD, in any combination and exclude thalidomide, lenalidomide and pomalidomide, derivatives thereof and analogs thereof, as well as any other agent identified as an IMiD, in any combination.

In some embodiments, the non-IMiD therapy can be a) bortezomib-dexamethasone (VD), b) bortezomib-cyclophosphamide-dexamethasone with daratumumab (CyBorD-Dara), c) bortezomib-cyclophosphamide-dexamethasone without daratumumab (CyBorD), d) carfilzomib-cytoxan-dexamethasone (Car-Cy-Dex), e) bortezomib-melphalan-prednisone with daratumumab (VMP-Dara), f) bortezomib-melphalan-prednisone without daratumumab (VMP), g) bortezomib-dexamethasone-cisplatin-Adriamycin-cyclophosphamide-etoposide (VD-PACE); and h) any combination of (a)-(g).

Unless otherwise defined, all technical terms used herein have the same meaning as commonly understood by one of ordinary skill in the art to which this disclosure belongs.

It is to be understood that the invention is not limited in its application to the details of construction and the arrangement of components set forth in the following description or illustrated in the following drawings. The invention is capable of other embodiments and of being practiced or of being carried out in various ways.

The following EXAMPLES provide illustrative embodiments. Certain aspects of the following examples are disclosed in terms of techniques and procedures found or contemplated by the present inventors to work well in the practice of the embodiments. In light of the present disclosure and the general level of skill in the art, those of skill will appreciate that the following examples are intended to be exemplary only and that numerous changes, modifications, and alterations can be employed without departing from the scope of the presently claimed subject matter.

EXAMPLES

Example 1: Peripheral Immune Profile and Minimal Residual Disease (MRD) Burden Following Autologous Stem Cell Transplantation (ASCT) in Multiple Myeloma (MM)

Patients and Methods. We studied peripheral NK, NK-T and T cell distribution/activation, and measured bone marrow MRD status by flow cytometry in 30 newly diagnosed MM patients 60+ days after ASCT. Patients were divided in 2 groups based on ica ratio and MM-plasma cell (MM-PC)

distribution: MRD$^{neg}$ (n=6), with κ/λ ratio ≤1.8 and MM-PC≤15 per million or MRD$^{pos}$ (n=24), with MM-PC>15 per million. Plasma was also collected from 17 of these patients (5 MRD$^{neg}$ and 12 MRD$^{pos}$) 60+ days after ASCT to quantify inflammatory cytokines, chemokines and growth factors by multiplex protein assay. Linear regression was used to determine association between each tested variable (25 by flow cytometry and 27 by multiplex protein assay) and MRD status. Unsupervised hierarchical cluster analysis was then applied to post-ASCT samples with selected variables that were differentially expressed between MRD$^{neg}$ and MRD$^{pos}$ patients (p<0.1) using complete linkage and Euclidean distances.

Results. More than a third of immune variables tested by flow cytometry (9/25) were significantly differential between MRD$^{pos}$ and MRD$^{neg}$ patients (p<0.1). Most significantly, MRD$^{pos}$ patients had fewer circulating CD56$^{high}$ NK cells than MRD$^{neg}$ (p=0.02). While NK cells had a propensity to be highly activated (90% NKG2D+) among MRD$^{pos}$ patients, they displayed an impaired killing phenotype with decreased KIR3DL1 expression compared with their MRD$^{neg}$ counterpart (p=0.01). NK-T and T cell distributions were not influenced by MRD status after ASCT, but phenotypically NK-T cells in MRD$^{pos}$ patients exhibited higher expression of NKG2D (p=0.05), but lacked NKG2A and Tim3 expression, indicative of greater mobilization. Plasma concentrations of all 27 soluble immune analytes tested were higher in MRD$^{neg}$ compared with MRD$^{pos}$ patients. Specifically, 2 pro-inflammatory cytokines [IL-12p70, IL-17] and 3 pro-angiogenic growth factors [FGF, PDGF, and VEGF] were highly correlated with MRD status (p<0.1). Unsupervised hierarchical clustering using all differentially expressed cellular and soluble immune markers showed better separation of MRD$^{neg}$ and MRD$^{pos}$ subgroups than using cellular or soluble immune markers separately (FIG. 1).

Conclusion. A comprehensive analysis of 52 immune variables assessing cytotoxic cell distribution, mobilization, killing potential, inflammatory status, immune polarization chemotaxis and angiogenesis revealed distinct differences in peripheral immunity between MRD$^{pos}$ and MRD$^{neg}$ MM patients after ASCT. Fewer circulating NK cells exhibiting a loss of killing potential characterized immune dysfunction among MRD$^{pos}$ patients. On the other hand, MRD$^{neg}$ patients more frequently displayed an inflammatory and pro-angiogenic cytokine profile. Taken together, these observations indicate that MRD represents a state of immune equilibrium where detectable or undetectable myeloma cells remain under surveillance by cellular and soluble immune mediators, and that this peripheral immune profile can be used as a predictor for MRD negativity.

Example 2: Peripheral Immune and Cytokine Profiling Correlates with Minimal Residual Disease (MRD) Status After Autologous Stem Cell Transplantation in Multiple Myeloma (MM)

Subjects and Methods. Newly diagnosed multiple myeloma patients treated at our institute with induction, ASCT and IMiD-based maintenance therapy according to standard clinical pathways were the subjects for this prospective study. We collected blood and bone marrow specimens from these subjects after obtaining written informed consent on a specimen collection protocol that has been approved by the Institutional Review Board of the Levine Cancer Institute/Carolinas HealthCare System (Charlotte, N.C.).

Bone marrow and blood specimens were collected from each patient at baseline around Day +60 post ASCT before starting maintenance therapy. Blood specimens were then serially collected after 1 month, 3 months and 6 months of maintenance treatment. Bone marrow aspirates were processed freshly and tested for MRD. Plasma was aliquoted and stored at −80° C., and PBMCs were re-suspended in freezing medium (RPMI1640, 12.5% w/v human serum albumin, 10% v/v DMSO) and stored in liquid nitrogen Immune phenotyping as well as multiplex protein array for immune mediators was performed on stored and batched samples according to the methodology described below.

Figure 2:
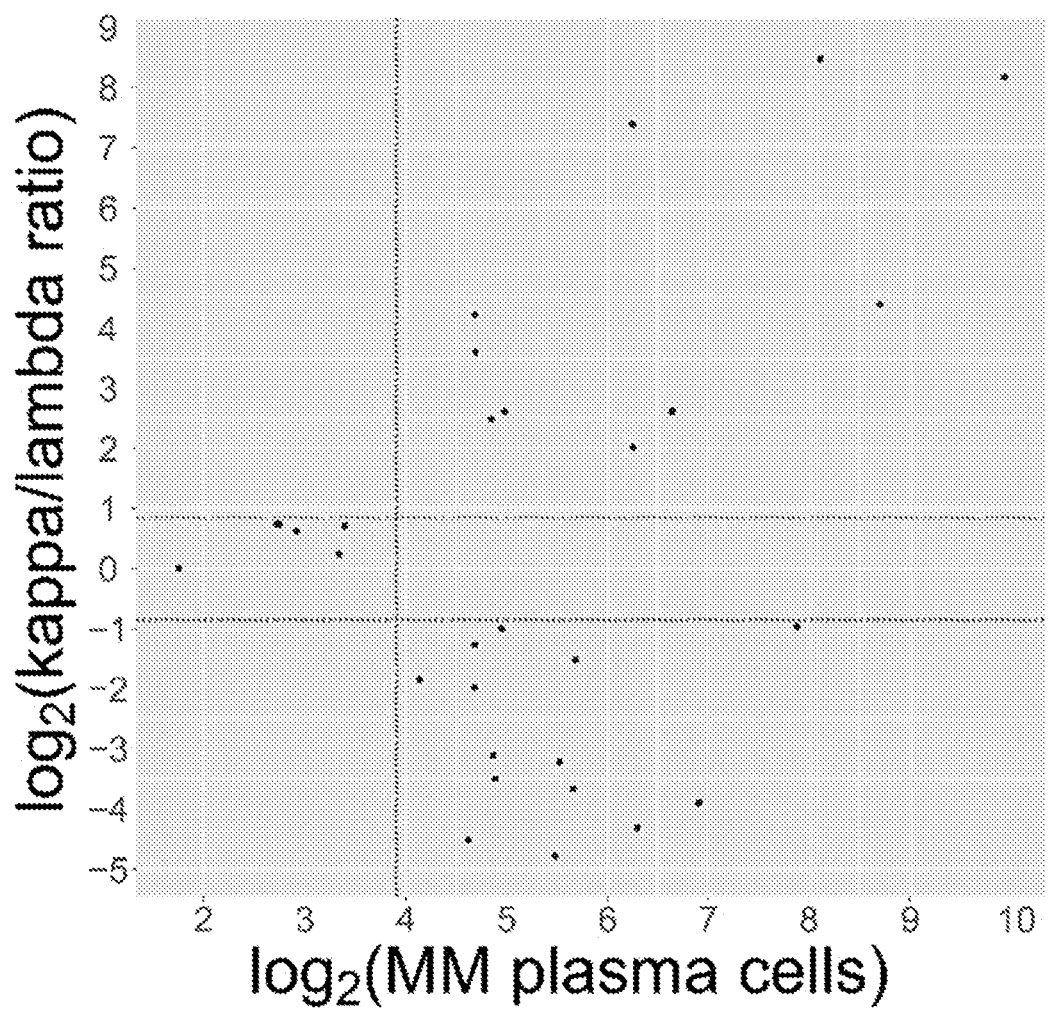
FIG. 2 depicts the division of 30 MM patients based on κ/λ ratio and MM-plasma cell (MM-PC) distribution: $MRD^{neg}$ (n=6), with κ/λ ratio ≤1.8 and MM-PC≤15 per million) or $MRD^{pos}$ (n=24), with MM-PC>15 per million.

MRD. Flow cytometry was performed according to the MRD assay developed and validated by the Euroflow consortium, with sensitivity established at 10$^{-5}$. Patients were divided in 2 groups based on κ/λ ratio and MM-plasma cell (MM-PC) distribution: MRD$^{neg}$ (n=6), with κ/λ ratio ≤1.8 and MM-PC ≤15 per million; or MRD$^{pos}$ (n=24), with MM-P C>15 per million (FIG. 2).

Figure 12:
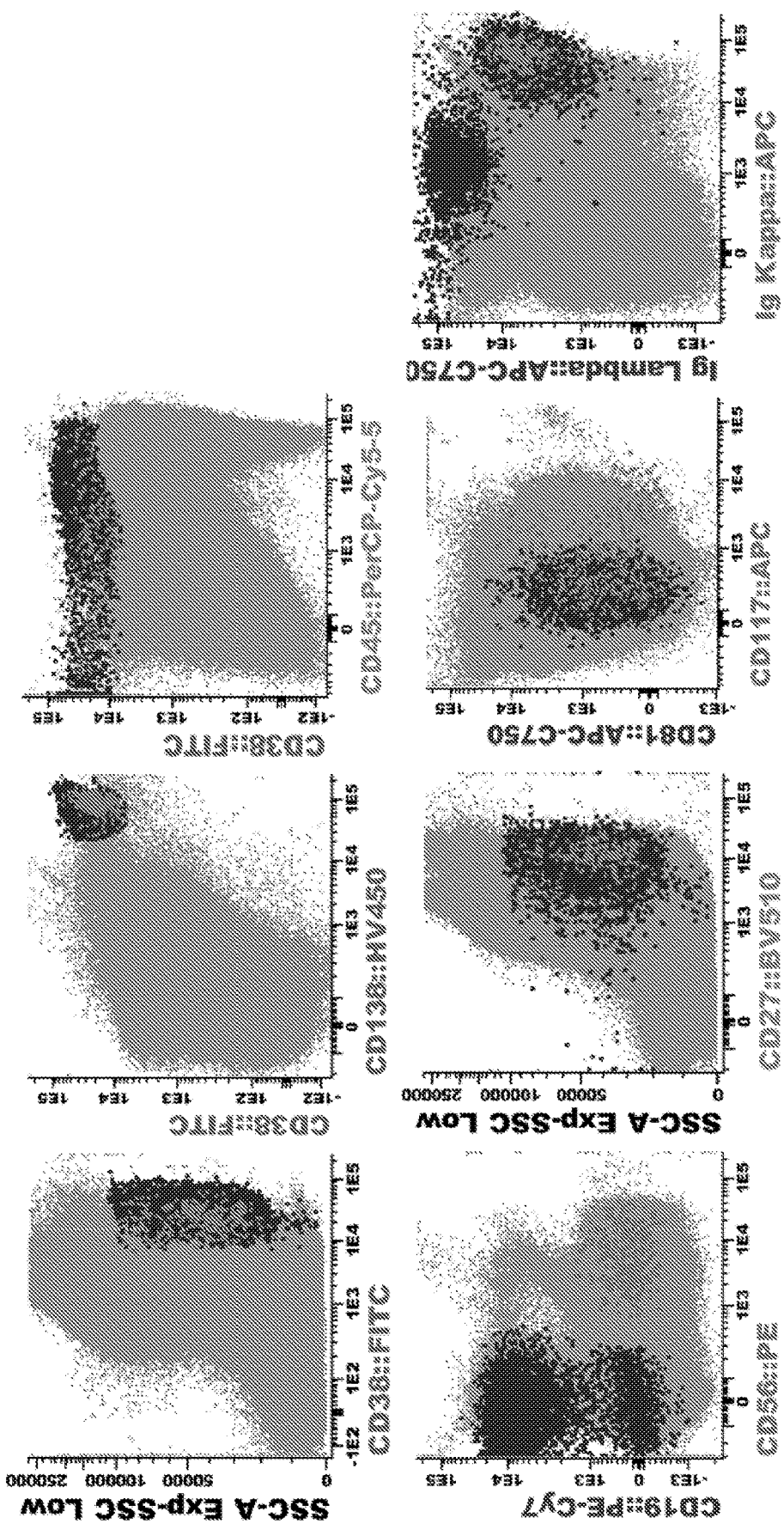
FIG. 12 shows representative flow cytometry data output and gating strategy for prospective assessment of NK, NK-T and T cell expansion activation and polarization. After red blood cell lysis, whole blood was stained for mature NK, NK-T-like and T cell lineage markers (respectively CD3$^-$ CD56$^{high}$, CD3$^+$ CD56$^-$) activation/functionality markers (KIR2DS4, KIR3DL1, NKG2A, NKG2D, NKp46) and markers of anergy (PD1, Tim3). At least 1 million nucleated events were acquired on a BD FACSAria II flow cytometer. Data were analyzed using the FlowJo version X software.

Immune phenotyping. Flow cytometry based enumeration and characterization of immune cell subsets in whole blood was performed by flow cytometry panel to determine T cell polarization and activation based on OMIP-17 methodology, and to determine NK cell, and inducible NK-T polarization based on OMIP-007 and OMIP-019 methodologies. Killer 'inhibitory' Ig-like receptors, (KiR2DS4, KiR3DL1) natural killer group 2 proteins (NKG2A, NKG2D) and natural killer p46 protein (NKp46) expression was quantified to assess polarization of NK, and NK-T cell. Flow cytometry data was acquired on a 10-color BD LSR Fortessa (and a 10-color BD FACSAria II), and analyzed using FlowJo version X software (FIG. 12).

Multiplex protein array (Bio-Plex). Plasma was also collected from 17 of these patients (5 MRDneg and 12 MRD-pos) 60+ days after ASCT to quantify inflammatory cytokines, chemokines and growth factors by multiplex protein assay. Concentrations of immune analytes in plasma was determined using a human custom 28-plex assay [15 cytokines (IL-1b, IL-2, IL-3, IL-4, IL-5, IL-6, IL-7, IL-9, IL-12p70, IL-13, IL-15, IL-17, IL-22, TNFa, INFg,); 5 chemokines (IL-8, MIP1a, MIP1b, MCP1, IP10); and 5 growth factors (VEGF, FGF, PDGF, EGF, HGF) and 3 markers of hypoxia and bone remodeling (IGF-1, HIF, RANK-L) following the manufacturer's instructions.

Statistics. Linear regression was used to determine association between each tested variable (25 by flow cytometry and 27 by multiplex protein assay) and MRD status. Unsupervised hierarchical cluster analysis was then applied to post-ASCT samples with selected variables that were differentially expressed between MRD$^{neg}$ and MRD$^{pos}$ patients (p<0.1) using complete linkage and Euclidean distances.

Results. More than a third of immune variables (9/25) tested by flow cytometry were significantly differential between MRD$^{pos}$ and MRD$^{neg}$ patients (p<0.1).

Figure 3:
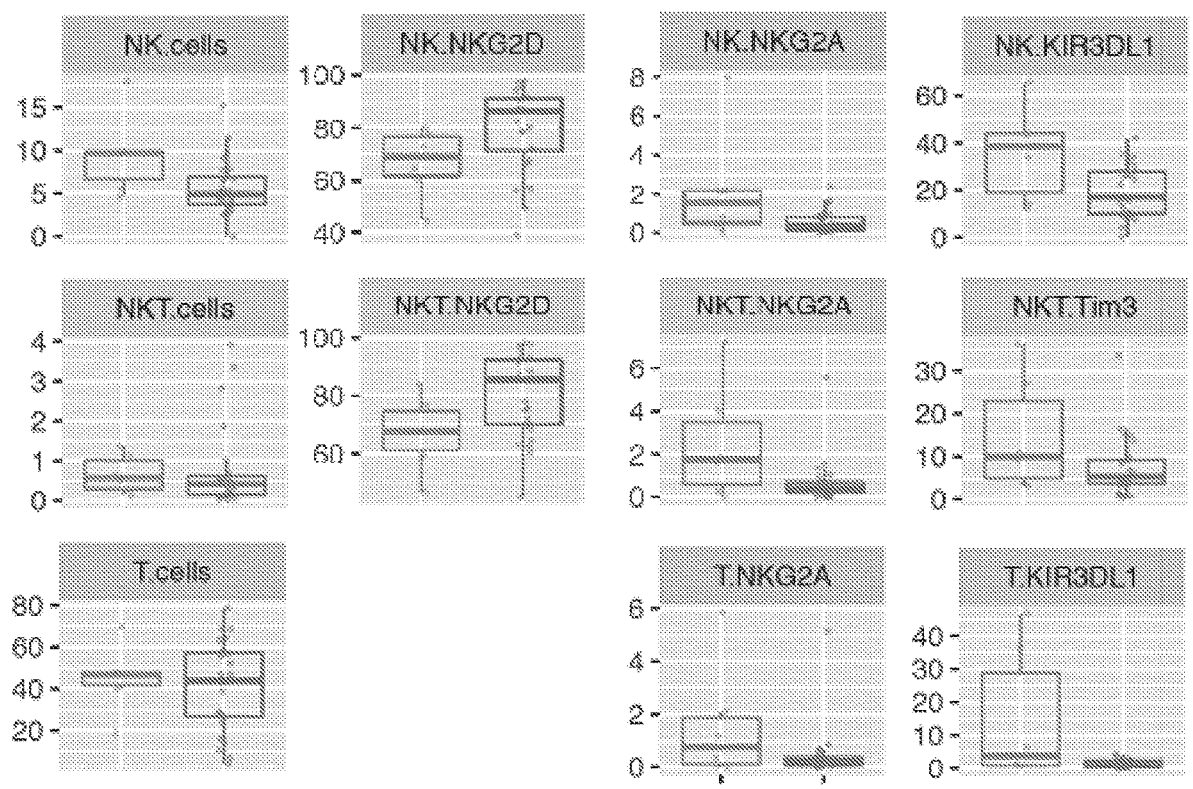
FIG. 3 depicts peripheral immune profiles of selected immune variables according to MRD status. For each profile, $MRD^{neg}$ is shown the left, and $MRD^{pos}$ is shown on the right.

MRD$^{pos}$ patients showed quantitative and qualitative defects of circulating NK cell (FIG. 3). MRD$^{pos}$ patients had comparatively lower number of CD56$^{high}$ NK cells than MRD$^{neg}$ (p=0.02). NK cells among MRD$^{pos}$ patients tended to be more activated, 90% expressed NKG2D among MRD$^{pos}$ vs. 70% in MRD$^{neg}$ (p=0.08). However, NK cell in MRD$^{pos}$ patients displayed impaired killing phenotype with decreased KIR3DL1 expression (p=0.01). Although the number of NK-T and T cell remained unaltered by MRD status post-ASCT, NK-T cell were more mobilized (high NKG2D expression but low NKG2A and Tim3 expression) in MRD$^{pos}$ (right) vs. MRD$^{neg}$ patients (left). MRD status: Negative (MRD≤15), left; Positive (MRD≥15), right.

Figure 4:
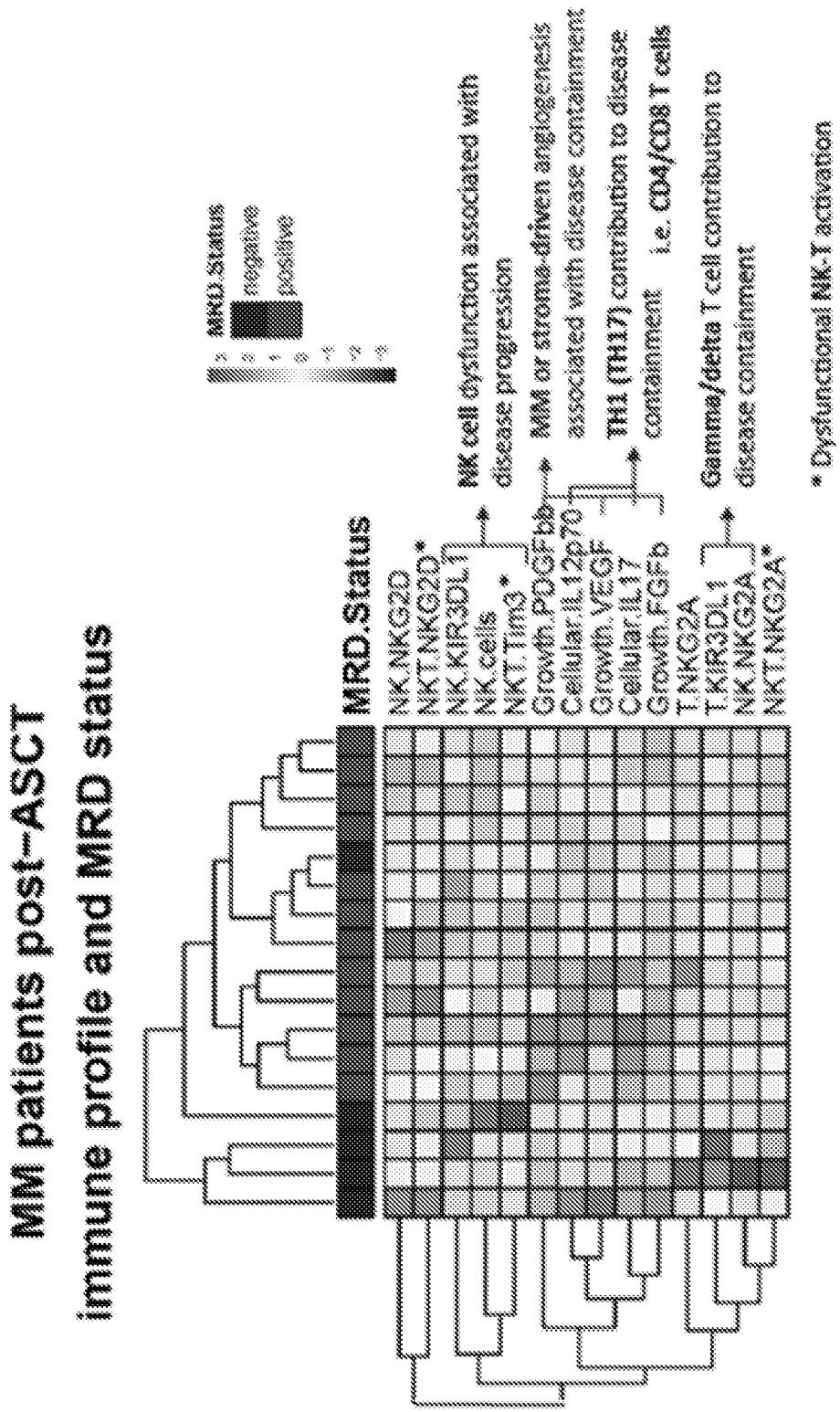
FIG. 4 depicts an expression profile heat map of selected peripheral immune markers differentiating $MRD^{neg}$ and $MRD^{pos}$ patients post-ASCT. Significant differences between $MRD^{neg}$ and $MRD^{pos}$ patients are noted.

Plasma concentrations of all 27 soluble immune analytes tested were higher in MRD$^{neg}$ compared with MRD$^{pos}$ patients, with 2 pro-inflammatory cytokines, IL-12p70, IL-17, and 3 pro-angiogenic growth factors, FGF, PDGF, and VEGF were highly correlated with MRD status (p<0.1). Unsupervised hierarchical clustering using all differentially expressed cellular and soluble immune markers showed better separation of MRD$^{neg}$ and MRD$^{pos}$ subgroups than using cellular or soluble immune markers separately (FIG. 4).

To our knowledge, this is the first study examining the influence of treatment (ASCT and lenalidomide maintenance) on the comprehensive immune repertoire in MM patients.

The follow up is yet short but our study provides new information on immune status between MRD$^{pos}$ and MRD$^{neg}$ MM patients after ASCT, and during lenalidomide maintenance therapy.

Example 3: Peripheral Immune Profile and MRD Status Following Autologous Stem Cell Transplantation in Multiple Myeloma Studies conducted demonstrated that MRD$^{pos}$ patients present immune dysfunction post-ASCT mostly centered around peripheral NC cell (and to a lesser extent NK-T cell) reduced expansion/killing potential. MRD$^{neg}$ patients do not have a silent immune system and show stronger TH1/17 immune polarization. Additional observations made include the following: Peripheral NK cells remain dysfunctional among MRD$^{pos}$ patients post-autologous stem cell transplantation (post-ASCT); MRD$^{neg}$ patients display potent TH1/17 responses post-ASCT; and following ASCT, adaptive cellular immunity remains activated among MRD$^{neg}$ patients.

Example 4: Effect of Immunomodulatory Drugs (IMiDs) on Immune Effectors After Autologous Stem Cell Transplantation (ASCT) in Multiple Myeloma Introduction. Patients with multiple myeloma have several phenotypic and functional immune aberrations that suppress host anti-myeloma immune responses. The degree and type of immune dysfunction can be targeted and reversed in many patients with active treatment. Therapies that result in deep and sustained remissions play a part in immunological control of disease in long-term responders. IMiD-mediated immunomodulatory effects conferring immune system reactivation have been reported in MM in the maintenance setting. We hypothesized that the circulating effector immune cell profile post-ASCT will be impacted by depth of response and IMiD based maintenance therapy.

Methods. Thirty MM patients who underwent ASCT and IMiD based maintenance and consented for specimen collection protocol were included in this study. Blood and bone marrow samples were collected before starting IMiD based maintenance therapy on Day 60+ post ASCT (time point defined as baseline). Blood samples were then serially collected after 1 month (T+1 mo, n=24), 3 months (T+3 mo, n=26) and 6 months (T+6 mo, n=19) of maintenance treatment. Multicolor flow cytometry was used for NK, NK-T and T cell distribution/activation immunotyping, and for measurement of bone marrow MRD status. Threshold for MRD positivity was established as $1.5 \times 10^{-5}$ abnormal/ clonal plasma cells. Clinical response assessment was performed post-ASCT at baseline per IMWG guidelines. Welsh two-sample t-test was used to compare immune profiles between MRDpos and MRneg groups, one-way ANOVA test to compare changes in immune profiles over time and Cox regression to correlate immune variables with progression free survival.

Figure 5:
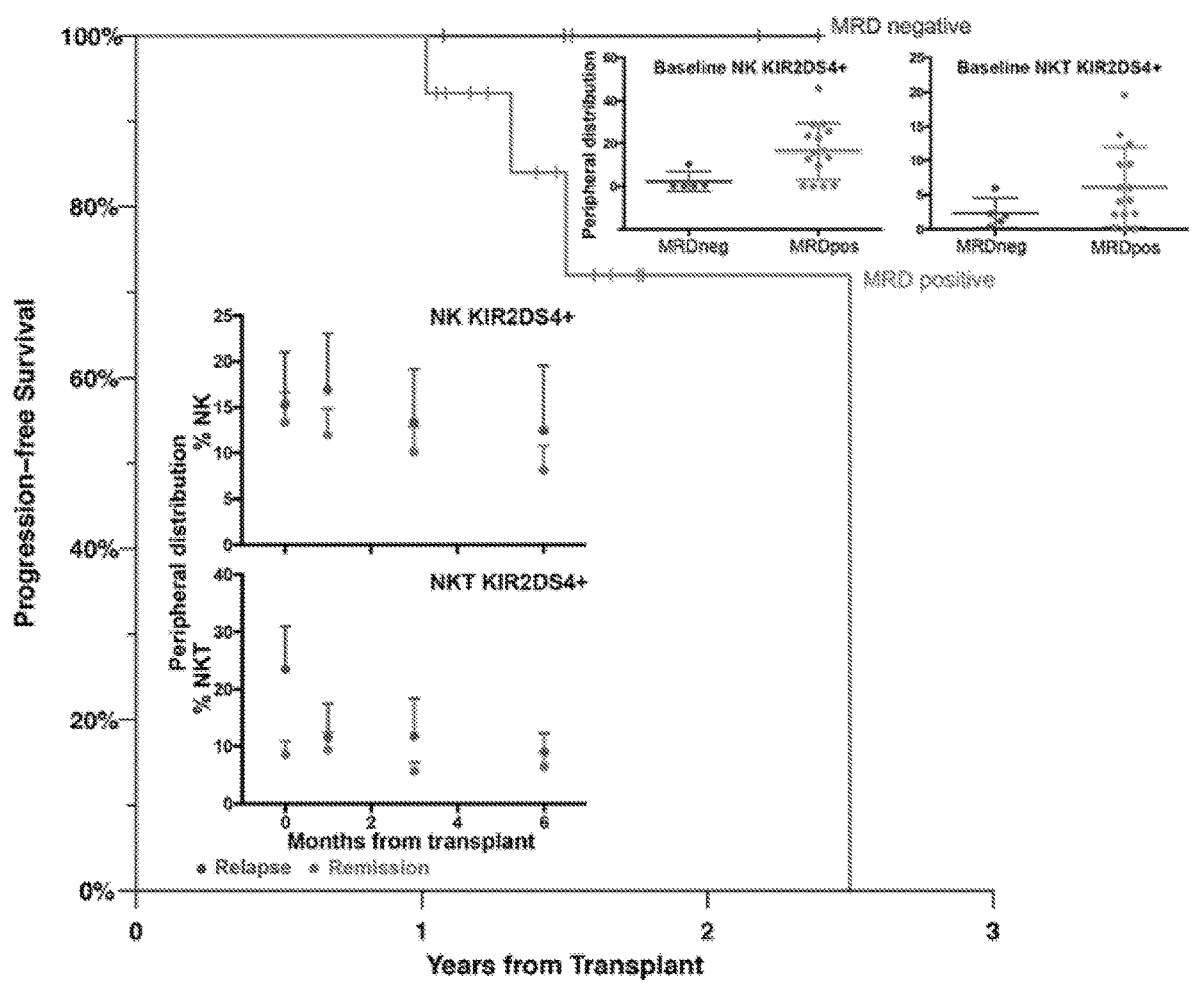
FIG. 5 shows KIR2DS4 expression by NK and NK-T cell as a marker of MRD status and progression free survival.

Results. In total, 16 patients achieved CR/sCR, 13 VGPR and 1 PR. MRD status was determined for 20 of 30 patients, 5 were MRDneg and 15 MRDpos. MRDpos patients had an immunotype characterized by higher expression of KIR2DS4 on NK (p=0.002) and NK-T cells (p=0.048) at baseline, compared with MRDneg patients. Twenty-six patients received single agent IMiD maintenance, 4 received IMiD/proteasome inhibitor combination. During IMiD maintenance therapy, NK and NK-T cell acquired phenotypes associated with greater effector functions as shown by increase in NK NKG2D+ (p=0.04), NK Tim3+ (p=0.049) and NK-T Tim3+ (p=0.01). T cells were marked by a NKG2D loss (p=0.0007) and Tim3 gain (p=0.0002) of expression. The median follow-up of the cohort was 19.3 months (IQR 14.8-21.3). Seven patients relapsed early within 12 to 24 months post-ASCT. High KIR2DS4 (HR=1.072, CI: 1.019-1.128; p=0.008), NKp46 (HR=1.050, CI: 1.004-1.098; p=0.031) and NKG2A (HR=1.222, CI: 1.018-1.466; p=0.032) expression by NK-T cells at baseline were associated with shorter PFS. NK and NK-T cells retained higher KIR2DS4 expression after 1, 3 and 6 mo of IMiD maintenance therapy in relapsing patients compared with those in remission (FIG. 5).

Conclusions. Our results demonstrate that KIR2DS4 expression by NK and NK-T cells is associated with MRD status post-transplant and also progression free survival under IMiD maintenance therapy. In complement with MRD status, this blood-based immunotype may therefore represent a valuable tool to identify patients less likely to benefit from current IMiD therapy(ies) and can be assessed longitudinally. Patients predicted to derive less clinical benefit from IMiDs could be offered alternative treatment regimens such as monoclonal antibodies, other immunotherapies or epigenetic therapy.

Example 5: Peripheral Cellular Immunome Reveals Heterogeneity Spanning Myeloma Spectrum Diseases Introduction. Progression from precursor states, termed monoclonal gammopathy of undetermined significance (MGUS) and smoldering multiple myeloma (SMM), to multiple myeloma (MM) is facilitated by cross-talk between malignant plasma cells and cellular/soluble components of the immunosuppressive bone marrow milieu, which promotes angiogenesis, bone destruction and immune-impairment. In support of this view, the frequencies of several peripheral immune cell subsets have been shown to be affected by the disease state. We hypothesized that beyond numerical alterations, activation and differentiation state of circulating innate and adaptive immune cell subsets determines progression from pre-malignant to malignant stage.

Methods. We compared multiple compartments of immune cell subsets in the peripheral blood samples of patients with MGUS (n=7), SMM (n=4) and MM (n=7) enrolled on an IRB-approved prospective biospecimen collection protocol of plasma cell disorders. Peripheral blood mononuclear cells obtained from each subject were immunophenotyped using two 14-color flow cytometry panels. Broadly, immune subsets surveyed included NK cell (mature and immature), NK-T cell, γδ T cell (δ9+γ2- and δ9-γ2-subsets), conventional CD4 and CD8 T cell (effector, effector memory and central memory) and regulatory T cell. Expression of activation, inhibition and maturation markers including NKG2A, NKG2D, KIR3D4, KIR2DS4, CD25, CD38, PD1, and Tim3 was analyzed in all relevant subsets. In total 62 immune variables (cell lineage and functional markers) were generated. For comparisons between MGUS, SMM and MM, one-way ANOVA test was used and p-values <0.1 were considered statistically significant. Unsupervised hierarchical cluster analysis was then applied to all samples with selected variables that were differentially expressed among three groups (p<0.1 by ANOVA) using WPGMA and Euclidean distances. Pair-wise comparisons between MGUS+SMM versus MM or MGUS versus SMM+MM were performed using Welsh two-sample t-test.

Figure 6:
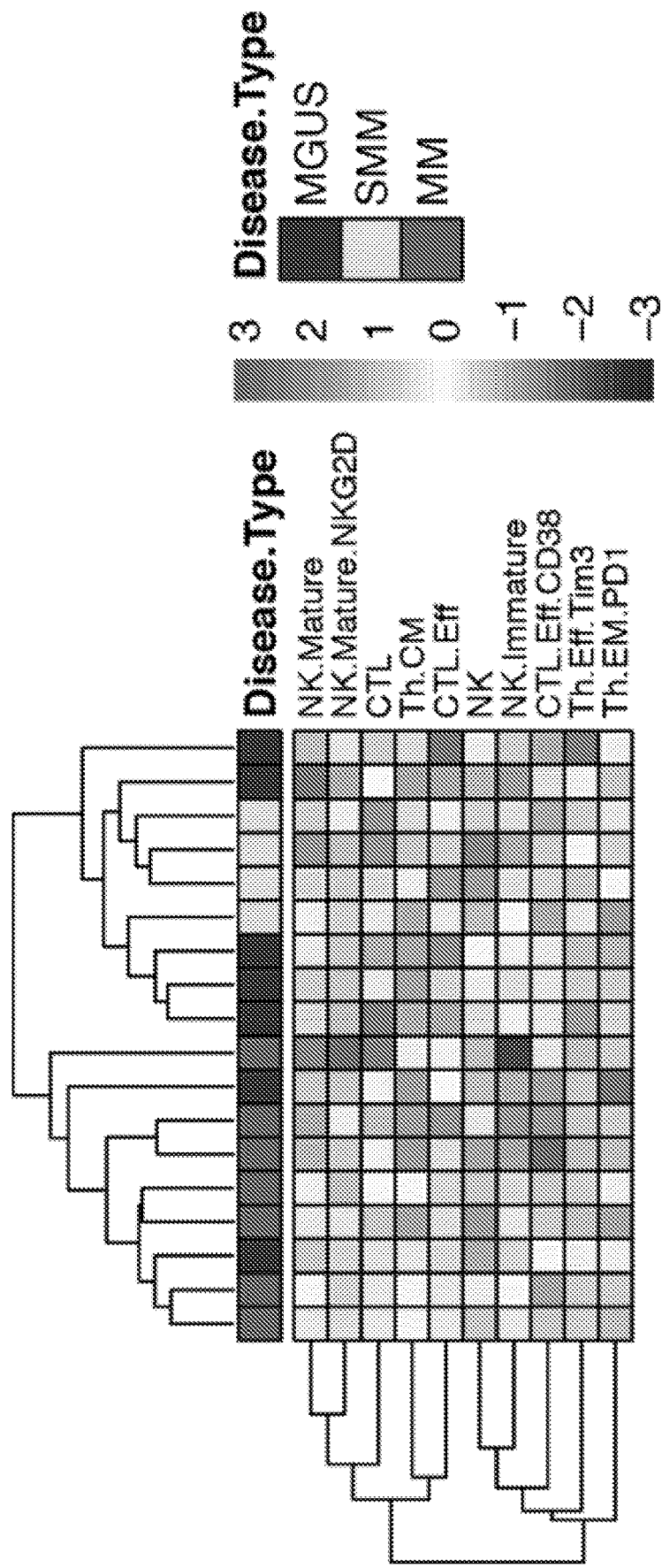
FIG. 6 depicts an expression profile heat map.

Results. Overall, distribution and functional state of 3 main immune cell lineages—NK cell, CD4+ T and CD8+ T cell—were altered across MGUS, SMM and MM (FIG. 6). Compared to subjects with MGUS and SMM, MM patients had fewer circulating NK cells (p=0.0069) with a noticeable shift in NK maturation (Immature/mature NK ratio 3/1 for MGUS and SMM vs. 1/1 for MM, p=0.0148). An immature NK phenotype was confirmed by higher expression of NKG2D on NK cell in MM patients (p=0.040). MGUS and SMM subjects shared an increased expression of immune checkpoints Tim3 (p=0.0046) and PD1 (p=0.0116) on peripheral CD4+ T effector and functional memory cells, compared with MM patients. Levels of circulating activated CD8 T effector cells were increased in SMM and MM patents compared with MGUS subjects (p=0.0007). Using the aforementioned functional markers, hierarchical clustering analysis segregated 7/7 MM patients and 9/11 MGUS and SMM subjects.

Conclusion. Transition from MGUS and SMM to MM is associated with systemic immune alterations in the functional state of innate (NK) and adaptive (CD4 and CD8 effectors) immune cell subsets. This proof of concept study suggests a role of the peripheral cellular immunome as a possible biomarker that might allow for identification of a subset of MGUS and SMM patients with a high risk of progression to active MM. We are evaluating this approach prospectively in a larger cohort of patients, including the clonality of the T cell repertoire.

Example 6: Peripheral Immune and Cytokine Profiling Correlates with Minimal Residual Disease (MRD) Status After Autologous Stem Cell Transplantation (ASCT) in Multiple Myeloma (MM)

MM patients receiving ASCT at our institution were enrolled between February 2015 and August 2016 with an IRB-approved specimen collection protocol for this prospective study. Bone marrow and blood specimens were collected from each patient between day +60 and +90 post ASCT before starting maintenance therapy. Bone marrow aspirates and blood were collected in sodium-heparin and K2-EDTA Vacutainer tubes respectively (BD Biosciences, San Jose Calif.) and freshly processed for MRD and immune phenotyping assays described below. Plasma was separated from blood by centrifugation (500 g, 10 min), aliquoted and stored at −80° C. Multiplex protein array for cytokine, chemokine and growth factor profiling was performed on stored and batched plasma samples per the methodology described below.

Minimal residual disease (MRD) flow cytometry assay. Flow cytometry for multiple myeloma MRD detection was performed based on the assay developed by the Euroflow consortium. Briefly, bone marrow aspirates were incubated post red blood cells (RBC) lysis (Pharm Lyse buffer, BD Biosciences, San Jose Calif.) in two separate tubes containing 10-marker antibody combinations staining for CD138, CD38, CD45, CD19, CD56, CD81, CD117, CD27, immunoglobulin κ and/or λ (Table 3). Both tube 1 and 2, containing 6 million cells each, were RBC lysed and stained for surface markers (30 minutes incubation at RT). Tube 2 was also fixed and permeabilized (Fix/Perm Permeabilization kit, Life Technologies, Carlsbad Calif.) for intracellular staining (15 minutes at RT). Five million events from each tube were acquired using a 14-color BD FACS Aria II flow cytometer (See Table 4 for configuration) for a total of 10 million cells assessed for MRD analysis. MRD Flow cytometry data were analyzed using Infinicyt version 1.8 (Cytognos S.L., Salamanca, Spain) software.

Figure 7A:
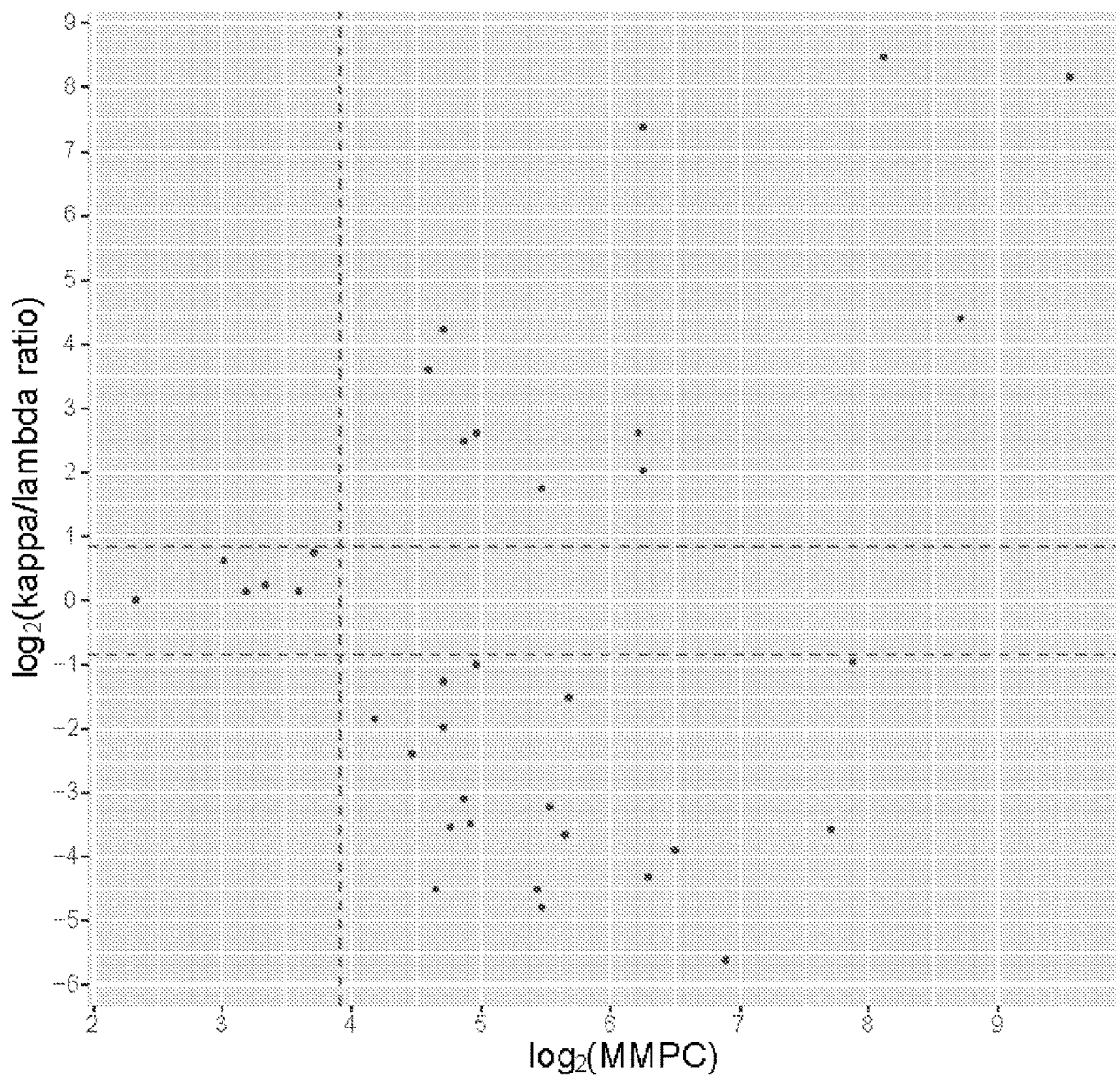
FIGS. 7A and 7B depict multiple myeloma minimal residual disease assessment and Kaplan-Meier plot of progression free survival. (A) Minimal residual disease was measured by flow cytometry 60 to 90 days post autologous stem cell transplant (ASCT). Cutoff value for MRD positivity was determined based on MM plasma cell count and κ/λ light chain ratio distributions. Patients were divided in 2 groups: $MRD^{neg}$ n=6 [absolute κ/λ ratio ≤1.8, and MM-PC≤15 per million] or $MRD^{pos}$, n=30 [MM-PC>15 per million]. (B) Kaplan-Meier estimates of progression free survival in $MRD^{neg}$ patients (blue) and $MRD^{pos}$ patients (red).
Figure 11:
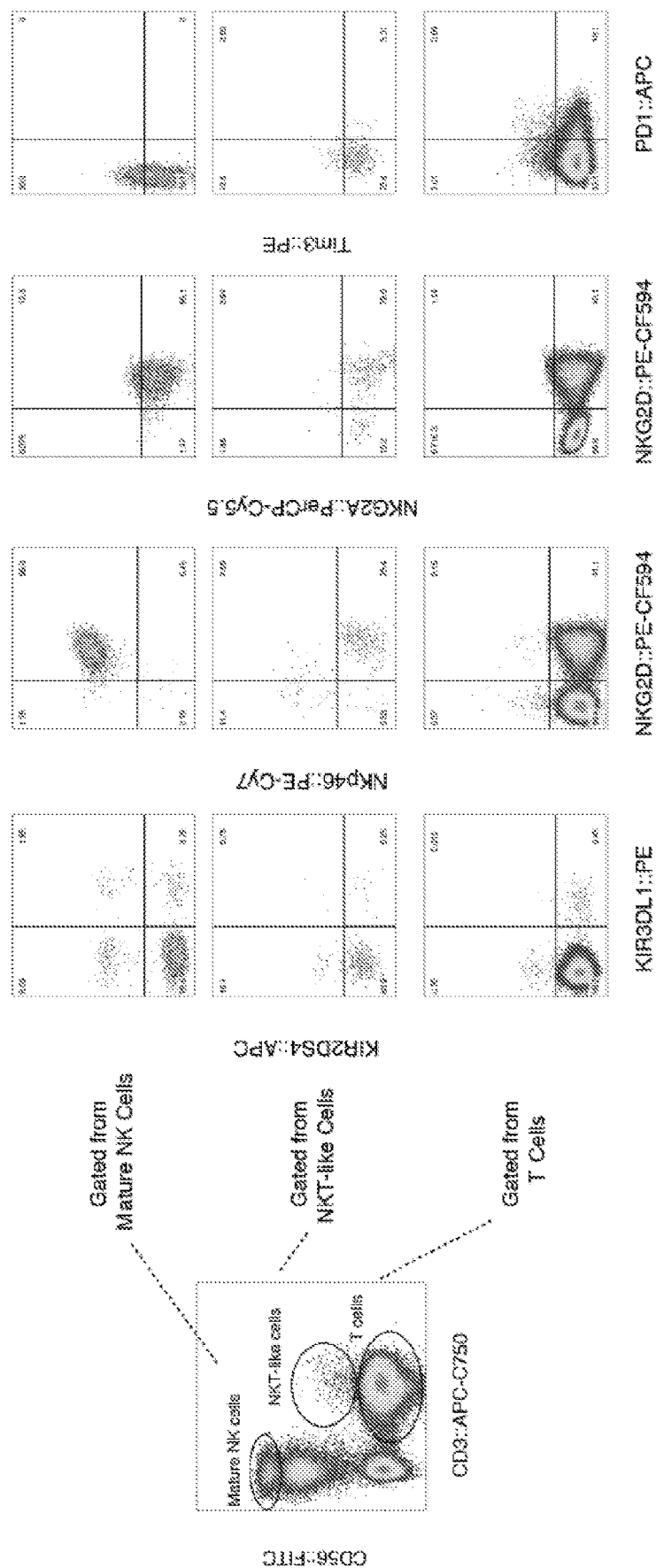
FIG. 11 shows representative flow cytometry data output and gating strategy for Minimal residual disease assessment. Following red blood cell lysis, bone marrow aspirates were in two separate tubes containing staining for PC/MM-PC phenotypic markers and PC clonality. Tube 1: CD38, CD138, CD45, CD19, CD56, CD27, CD81, CD117; Tube 2: CD38, CD138, CD45, CD19, CD56, CD27, Ig light chain κ and λ. At least 5 million nucleated events were acquired for each tube on a BD FACSAria II flow cytometer. Data were analyzed for each tube separately using Infinicyt version 1.8 software.

Multiple Myeloma—MRD definition. Plasma cells were gated from a $CD38^+$ $CD138^{high}$ population. Abnormal plasma cells were differentiated from normal plasma cells based on $CD45^{high}$, $CD19^{-/low}$, $CD56^{high}$, $CD81^-$, $CD117^+$ and/or $CD27^{int}$ phenotype (FIG. 11). Threshold for MRD positivity for this study was established at $1.5 \times 10^{-5}$ (e.g., >15 abnormal PC in 1 million nucleated cells) with kappa/lambda ratio >1.2 (FIG. 7A).

Immune phenotyping. Enumeration and characterization of immune cell subsets in whole blood was performed to determine NK cell, inducible NK-T, and T cell activation and polarization based on OMIP-007, OMIP-017 and OMIP-019 methodologies. Surface expression of lineage markers (CD3 and CD56), Killer 'inhibitory' Ig-like receptors (KiR2DS4, KiR3DL1), natural killer group 2 proteins (NKG2A, NKG2D), natural killer p46 protein (NKp46), Programmed death receptor 1 (PD1) and T-cell inhibitory receptor (Tim3) expression were assessed by flow cytometry Immune phenotyping flow cytometry data were acquired on a 14-color BD FACSAria II, and analyzed using FlowJo version X software.

Multiplex protein array (Bio-Plex). Plasma collected 60 to 90 days post-ASCT was used to quantify inflammatory cytokines, chemokines and growth factors by multiplex protein assay. Concentrations of immune analytes in plasma was determined using a human cytokine 27-plex assay: 14 cytokines (IL-1β, IL-1ra, IL-2, IL-4, IL-5, IL-6, IL-9, IL-10, IL-12, IL-13, IL-15, IL-17, IFN-γ, TNF-α); 7 chemokines (Eotaxin, IL-8, IP-10, MCP-1, MIP-1α, MIP-1β, RANTES); and 6 growth factors (IL-7, FGF basic, G-CSF, GM-CSF, PDGF-BB, VEGF) (Bio-Rad, Hercules, Calif., USA), as described in Steuerwald et al. Briefly, samples were diluted 1:4 (v:v) in sample diluent and incubated for 30 minutes (300 rpm agitation at room temperature) with capture antibody-coupled magnetic beads. Following three washes in a Bio-Plex Pro wash station, samples were incubated for 30 minutes in the dark (300 rpm agitation at room temperature) with biotinylated detection antibody. Each captured analyte was detected by the addition of streptavidin-phycoerythrin and quantified using a BioPlex array reader. Analyte concentrations were calculated with Bio-Plex Manager software.

Statistics. For markers tested by flow cytometry, Student's t-test was used to compare differences between $MRD^{neg}$ and $MRD^{pos}$ groups. For markers tested by multiplex protein assay, Mann-Whitney U test was used to compare differences between $MRD^{neg}$ and $MRD^{pos}$ groups. Unsupervised hierarchical cluster analysis was then applied to post-ASCT samples with selected variables that were differentially expressed between $MRD^{neg}$ and $MRD^{pos}$ patients using WPGMA and Euclidean distances. Progression-free survival (PFS) was defined as the time from ASCT to first event, which was defined as relapse, progression or death. Observation of patients was censored at the time of last contact, when no events were observed. The Kaplan-Meier method was used to estimate probabilities of PFS.

Figure 7B:
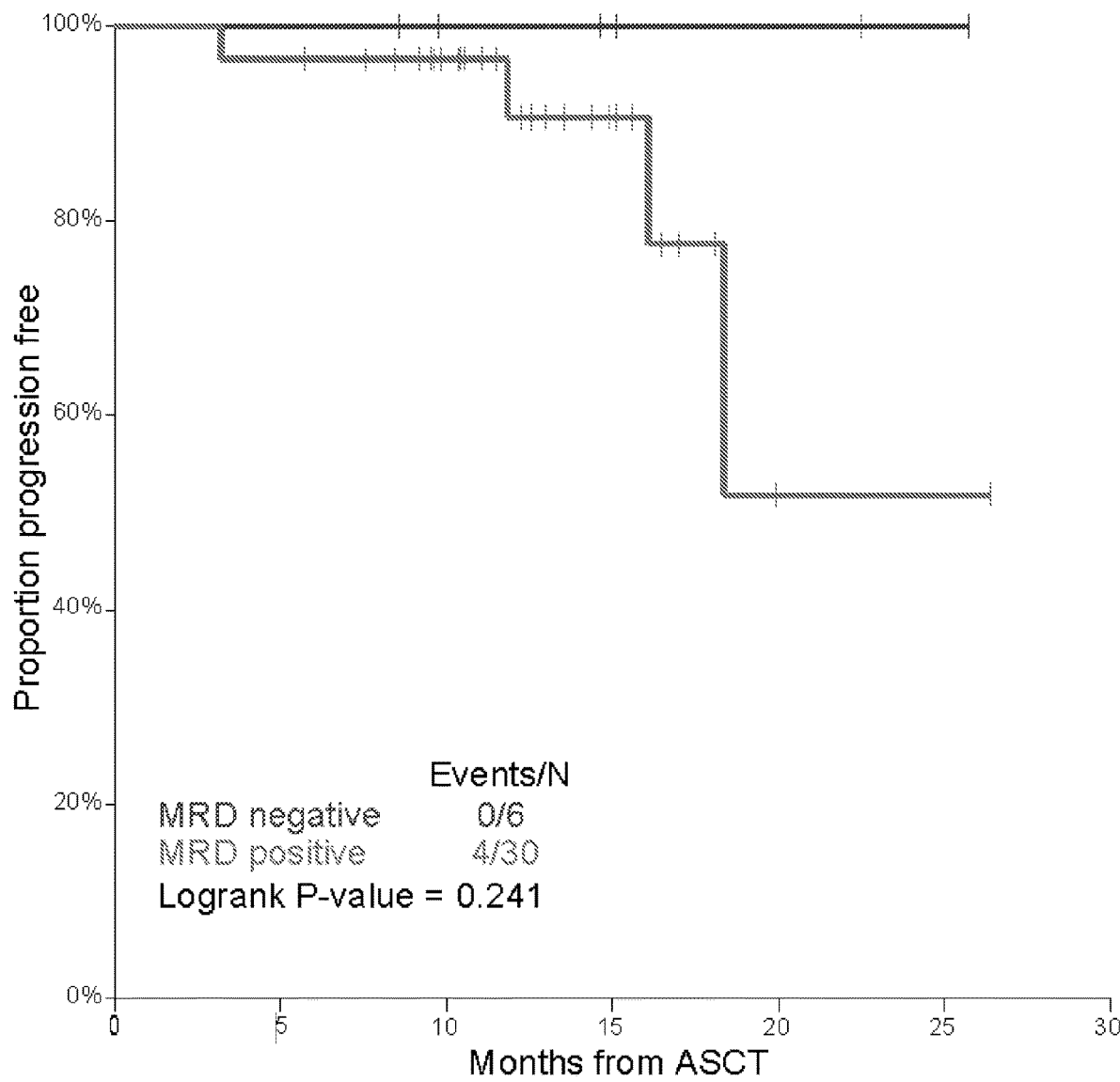

Patient Characteristics. Thirty-six multiple myeloma patients were enrolled in the study, 31 newly diagnosed and 5 relapsed. Six (16.7%) were $MRD^{neg}$ and 30 (83.3%) were $MRD^{pos}$ around day +60 post-ASCT. Demographics and clinical information for $MRD^{neg}$ and $MRD^{pos}$ subjects is provided in Table 1. All patients received a proteasome inhibitor based induction regimen, 25 patients (70%) were treated with proteasome inhibitor and immune modulatory drugs (IMiDs) based induction (Table 2). At a median follow up of 13 months (interquartile range, 9.9-16.5 months), none of the $MRD^{neg}$ patients had relapsed, while 4 of 30 $MRD^{pos}$ patients had progressed (FIG. 7B). However, it's still too early to show a significant difference for PFS between $MRD^{neg}$ and $MRD^{pos}$ groups.

Figure 8A:
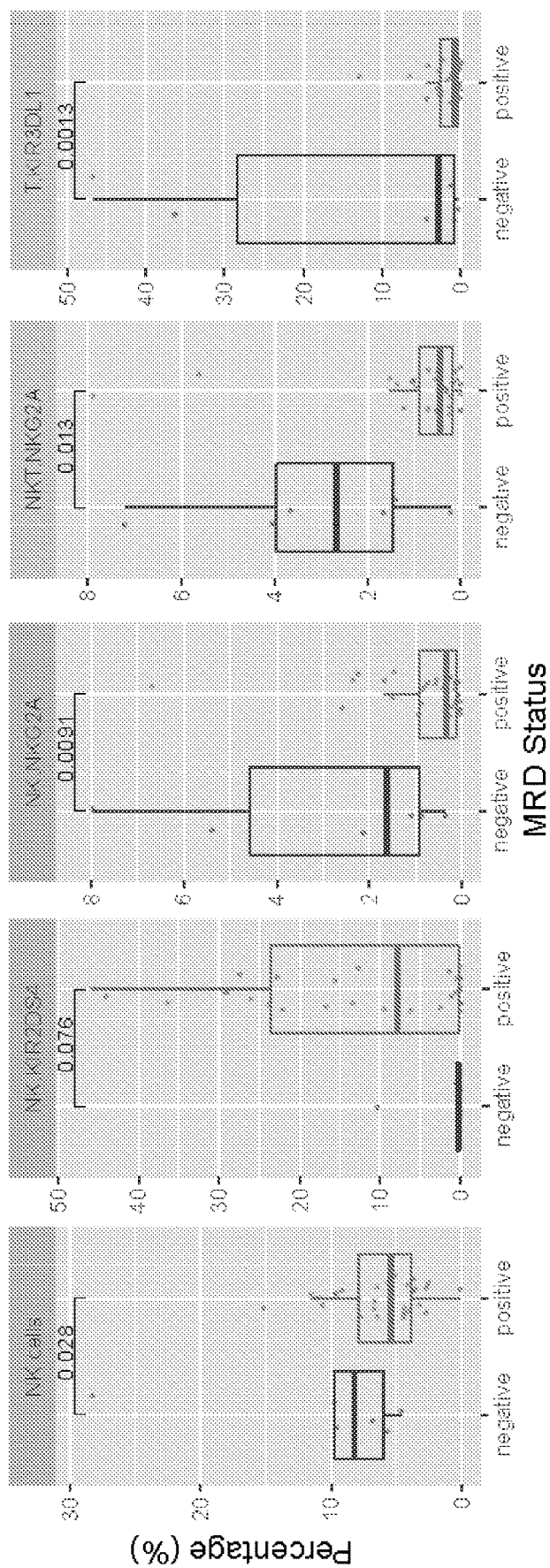
FIGS. 8A and 8B depict Peripheral immune profile according to MRD status. (A) Box plots of mature NK cells, NK cell KIR2DS4 and NKG2A expression, NKT-like cell NKG2A expression and T cell KIR3DL1 expression in $MRD^{neg}$ and $MRD^{pos}$ patients, showing these 5 peripheral immune markers were associated with MRD status (p<0.1). Measurements for $MRD^{neg}$ patients are represented in blue and $MRD^{pos}$ patients are represented in red. (B) Hierarchical clustering and heat map of the 5 differentially expressed peripheral immune markers in 36 patients. Markers with comparatively low expression values are shown using shades of blue and high expression values are represented using shades of red. Clustering at the level of individual patients is represented by the dendrogram at the top, with the blue color bar under the dendrogram indicating MRD$^{neg}$ patient and the red color bar indicating MRD$^{pos}$ patient.

Significant alteration of peripheral mature NK cell compartment in MM patients with $MRD^{pos}$ response after ASCT. We investigated the association between MRD status and peripheral innate and adaptive immune activation. Peripheral distribution of lymphoid cell subsets with killing potential, namely mature NK cell ($CD56^{high}$ $CD3^-$), NKT-like cell ($CD56^+$ $CD3^+$) and T cell ($CD56^-$ $CD3^+$) was determined by flow cytometry analysis. Phenotypic markers of maturation, activation, functionality and anergy were analyzed on NK, NKT and T cell. The results showed significant alteration of peripheral mature NK cell compartment between $MRD^{neg}$ and $MRD^{pos}$ MM patients. Patients with $MRD^{pos}$ status had fewer circulating NK cells (6.1±0.6% vs. 10.8±3.6%, p=0.028) (FIG. 8A). Though NK cell numbers among lymphocytes was reduced in $MRD^{pos}$ patients, there was no difference in the activation status of NK cells between $MRD^{neg}$ and $MRD^{pos}$ subgroups as elicited by expression of activating receptor NKG2D in >75% of NK cells in both the groups. However, $MRD^{pos}$ patients displayed increased expression of activation receptor KIR2DS4 (12.9±2.6% vs. 1.9±1.7%, p=0.076) and a reduced expression of inhibitory receptor NKG2A (0.9±0.2% vs. 3.0±1.2%, p=0.009) compared with their $MRD^{pos}$ counterpart.

To a lesser extent NKT-like and T cell pool was also altered between $MRD^{neg}$ and $MRD^{pos}$ MM patients post-ASCT. Although peripheral distribution of NKT-like cell was not significantly different (p=0.689), $MRD^{pos}$ patients lacked a peripheral NKT-like cell subset expressing NKG2A (0.9±0.3% vs. 3.0±1.0%, p=0.013) and T cell subset expressing KIR3DL1 (1.9±0.5% vs. 15.0±8.5%, p=0.013) (FIG. 8A). Additional characterization of T cell subset expressing KIR3DL1 in multiple myeloma patients showed that this subset of T cells is not derived from T helper ($CD3^+$ $CD4^+$) or cytotoxic T cells ($CD3^+$ $CD8^+$), rather exclusively from γδ T cells ($CD3^+$ $CD56^-$ pan-γδ$^+$; specifically, Vγ9$^+$δ2$^-$ and Vγ9$^-$δ2$^-$).

Figure 8B:
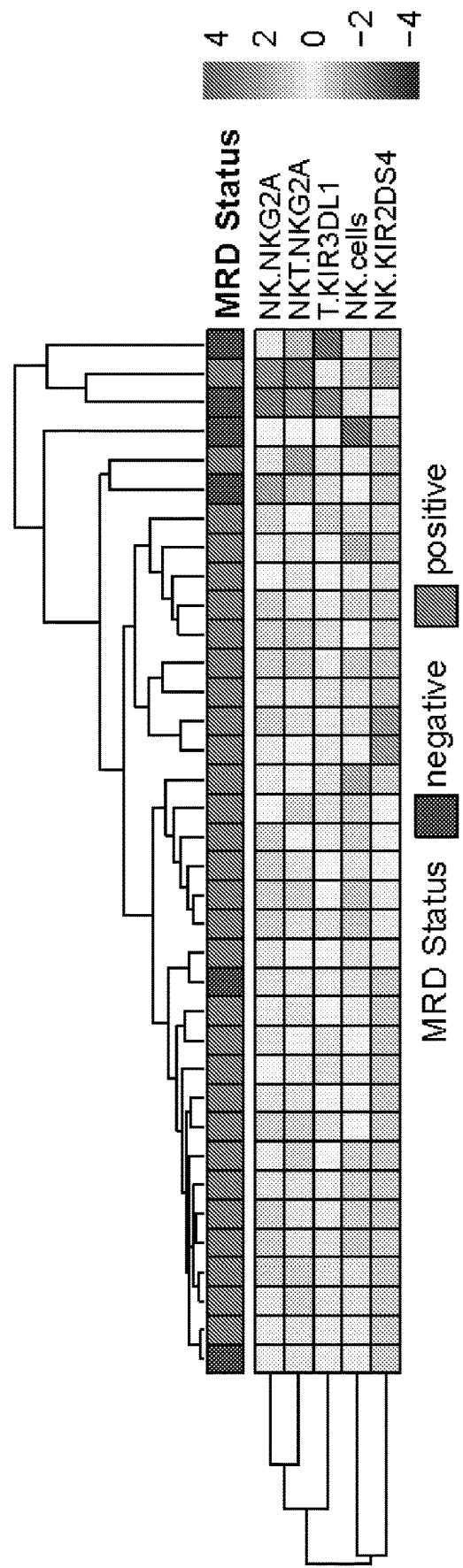

Unsupervised hierarchical clustering was performed using the 5 peripheral immune markers, including mature NK cell distribution, mature NK cell KIR2DS4 and NKG2A expression, NKT-like cell NKG2A expression and T cell KIR3DL1 expression, which were differentially expressed between $MRD^{neg}$ and $MRD^{pos}$ patients. It allowed clustering of 4/6 (66.6%) of $MRD^{neg}$ patients and 28/30 (93.3%) $MRD^{pos}$ patients (FIG. 8B).

Limited alteration of peripheral immune polarization and chemotaxis markers in MM patients with $MRD^{pos}$ response. In addition to peripheral immune phenotyping post-ASCT, plasma concentrations of soluble immune analytes (cytokines, chemokines and growth factors) were quantified by multiplex protein array in 32/36 patients enrolled in the study. Five had tested $MRD^{neg}$ and 27 $MRD^{pos}$ by flow cytometry.

Cytokine and chemokines were quantified to characterize immune polarization (TH1/2, TH9/17) and chemotaxis events respectively. Plasma concentrations of growth factors associated with MM were also compared between $MRD^{neg}$ and $MRD^{pos}$ patients.

Figure 9:
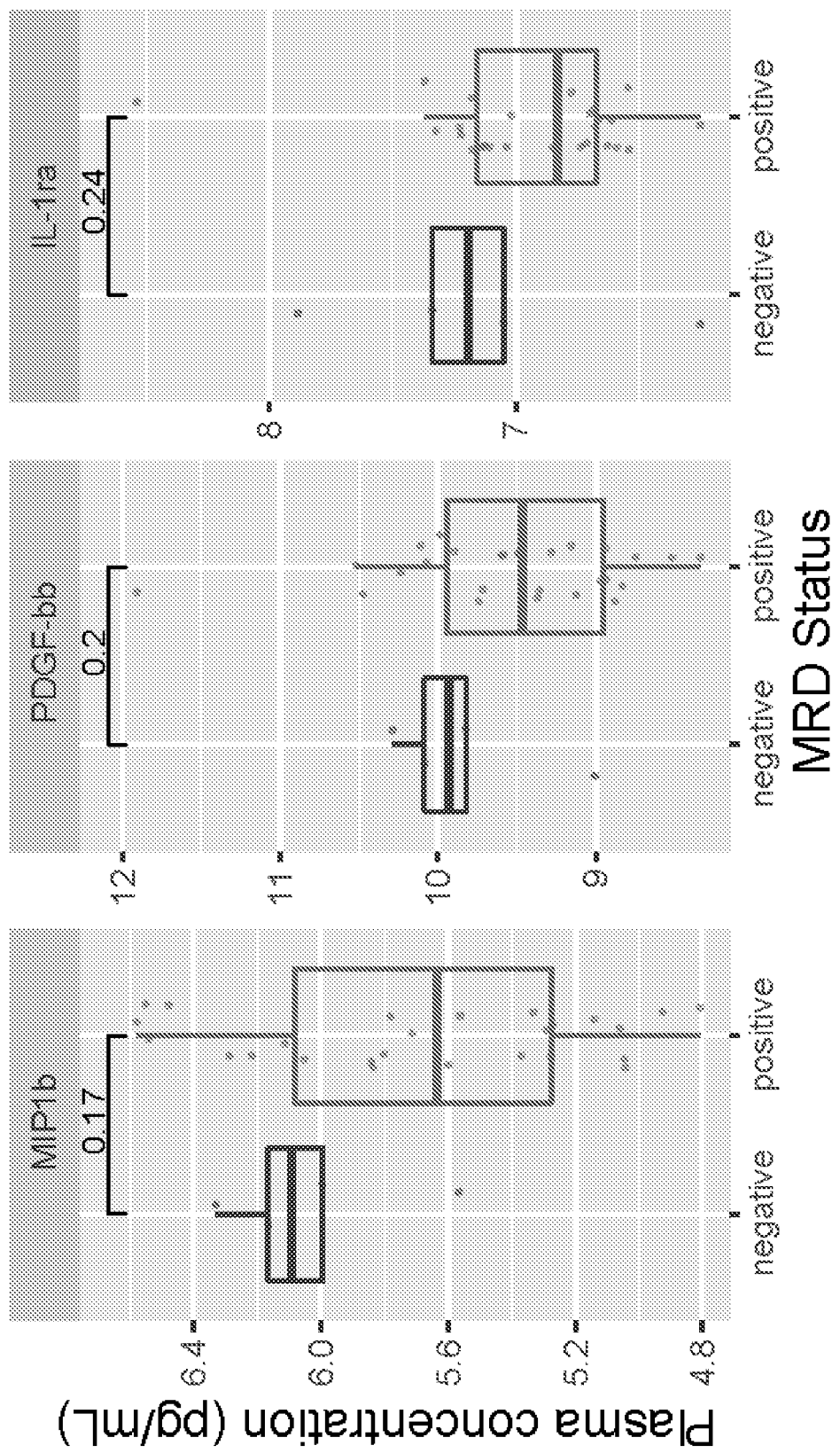
FIG. 9 depicts soluble immune variables associated with MRD status. Box plots of MIP1b, PDGF-bb and IL-1ra in MRD$^{neg}$ and MRD$^{pos}$ patients, showing these 3 plasma protein were potentially associated with MRD status (p<0.25). Measurements for MRD$^{neg}$ patients are represented in blue and MRD$^{pos}$ patients are represented in red.

Two cytokines, IL-2 and IL-15 were not detected in plasma of MM patient post-ASCT (data not shown). Plasma concentrations of the remaining 25 soluble immune analytes tested were highly heterogeneous across the entire cohort and none were significantly differentially expressed between $MRD^{neg}$ and $MRD^{pos}$ patients (p>0.1). To investigate soluble immune variable most closely associated with MRD status, the top 3 plasma proteins potentially discriminating $MRD^{neg}$ and $MRD^{pos}$ patients (p<0.25) were selected (FIG. 9). Macrophage Inflammatory protein-1β (MIP1b/CCL4), platelet-derived growth actor homodimer (PDGF-bb) and Interleukin-1 receptor antagonist (IL-1ra) plasma concentrations tend to be lower among $MRD^{pos}$ patients.

Figure 10A:
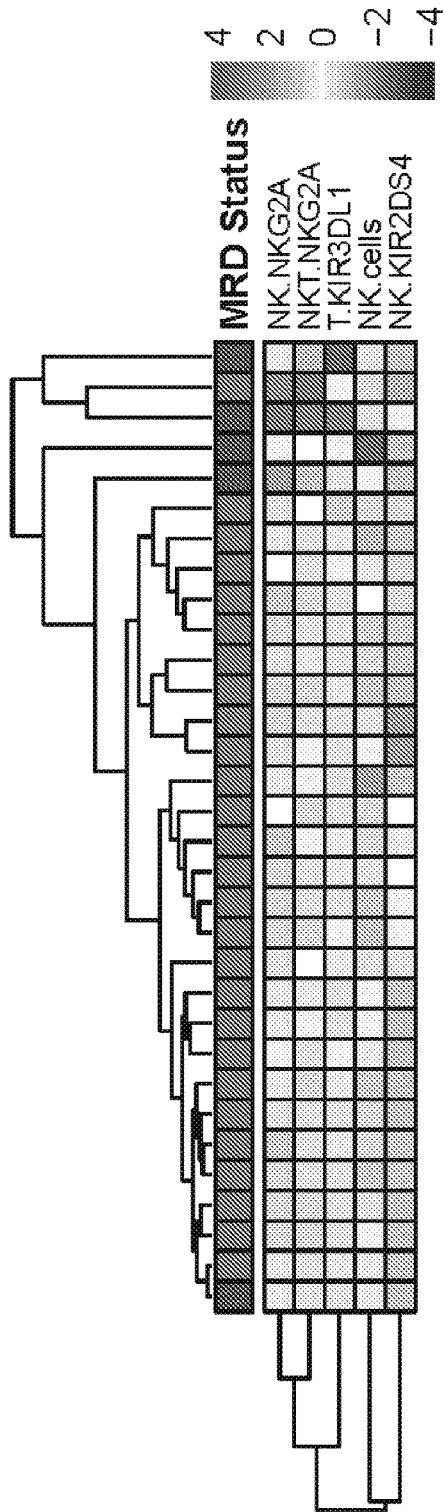
FIGS. 10A and 10B depict hierarchical clustering and heat map of differentially expressed peripheral immune markers and soluble immune variables in 32 patients. Thirty-two out of 36 patients enrolled in the study had comprehensive immune profiles established combining 25 peripheral immune markers quantified by flow cytometry and 27 soluble immune variables quantified by multiplex protein assay. (A) Hierarchical clustering and heat map base on 5 differentially expressed peripheral immune markers (mature NK cell distribution, NK cell KIR2DS4 and NKG2A expression, NKT-like cell NKG2A expression and T cell KIR3DL1 expression). (B) Hierarchical clustering and heat map base on 5 aforementioned differentially expressed peripheral immune markers and 3 soluble immune variables (MIP1b, PDGF-bb, IL-1ra). Markers/variables with comparatively low expression values are shown using shades of blue and high expression values are represented using shades of red. Clustering at the level of individual patients is represented by the dendrogram at the top, with the blue color bar under the dendrogram indicating MRD$^{neg}$ patient and the red color bar indicating MRD$^{pos}$ patient.
Figure 10B:
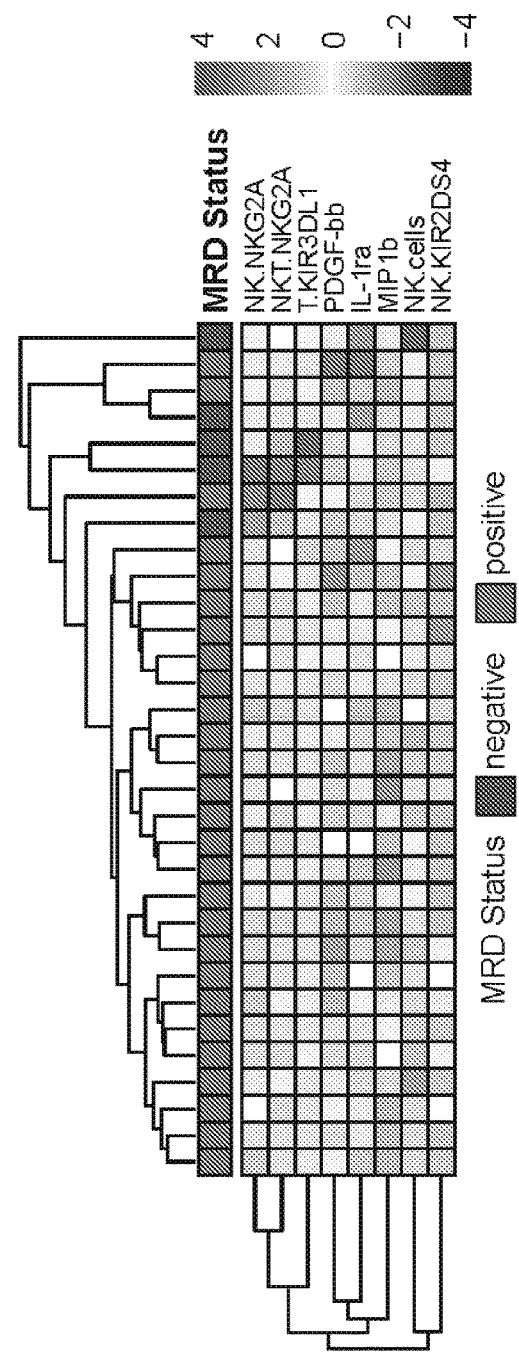

Unsupervised hierarchical clustering was performed on 32 patients with both peripheral immune phenotyping and plasma protein profiling tested. Using the 5 peripheral immune phenotypic markers differentially expressed under different MRD status (markers in FIG. 8A) allowed clustering of 4/5 (80%) $MRD^{neg}$ and 26/27 (96.3%) $MRD^{pos}$ patients (FIG. 10A). Adding the top 3 plasma protein variables associated with residual disease burden (variables in FIG. 9) moved all 5 $MRD^{neg}$ patients adjacent in the dendogram, along with 3 $MRD^{pos}$ patients (FIG. 10B).

Treatments resulting in deep durable remission and eradication of MRD have significantly improved outcomes and sparked interest in studying the immune profiles governing therapy response and resistance. In this study, using a comprehensive immune profiling of 52 immune variables in peripheral blood assessing cytotoxic cell distribution, mobilization, killing potential and polarization, we showed that five flow cytometry-based markers including mature NK cell number, mature NK cell KIR2DS4 and NKG2A expression, T cell KIR3DL1 expression, and NKT-like cell NKG2A expression differentiated $MRD^{neg}$ MM patients from $MRD^{pos}$ patients after ASCT. To our knowledge, this is the first study focused on comprehensive evaluation of immune cell subsets and cytokine/chemokine effectors in MM to determine the influence of immune profiling on MRD. This study sheds light on some of the immune mechanisms that may be playing role in eradication of MRD.

Our data suggest a relative balance of cell surface receptors that deliver either inhibitory or activating signal on NK cells may be important in mediating MRD negative status. NK cells contribute to innate immune defenses via direct cytotoxicity and the secretion of cytokines and chemokines. NK cell recovery both in number and function is quick after ASCT, generally within one month. In our study, $MRD^{neg}$ patients had more NK cells compared with $MRD^{pos}$ patients two months after ASCT. Consistent with our results, an increase in effector CD8+ T cell and NK cells has been previously described for MM patients in long-term disease control, suggesting the protective role of cytotoxic cells in controlling tumor growth. While the absolute number of NK cells was significantly higher in patients with $MRD^{neg}$ response, NK cell population in these patients displayed lower expression of activating receptors KIRDS4 and increased expression of inhibitory molecules NKG2A compared with the $MRD^{pos}$ group. It is possible that the absolute number of NK cell exerting a continuous cytotoxic effect is important, and once myeloma cells are contained to the level of $MRD^{neg}$ state, the activating signals on the NK-cell are downregulated. Consistent with our findings, in a small study of 13 MM patients who remained in CR for more than 6 years after ASCT, investigators observed fewer activating receptors like NKP46 together with a trend of increased expression of inhibitory molecules NKG2A and KIR2DL1 on NK cells compared to controls.[17] Accordingly, these observations provide evidence that NK cell based immune surveillance may contribute to long-term disease control in MM.

We observed significantly lower frequencies of T cell subset displaying KIR3DL1 in $MRD^{pos}$ vs. $MRD^{neg}$ patients. KIR3DL1 is one of the highly polymorphic transmembrane receptor of the KIR family that mediates inhibition of NK cell mediated cell cytotoxicity and cytokine production. KIR3DL1 is also expressed on a small proportion of T cell population including γδ T cells, where it has shown to inhibit γδ T cells and also protect these cells from cell death by preventing the up-regulation of Fas ligand. Even though the flow panel designed for this study did not allow us to provide a direct evidence of γδ T cells, by using an expanded flow cytometry sorting panel, we showed the T cell subset displaying KIR3DL1 indeed belongs to the γδ T cells and not to the classical CD4+ helper T cells or CD8+ cytotoxic T cells (unpublished data). Extrapolation of this key observation into current work would suggest that $MRD^{pos}$ patients had reduced number of γδ T cells.

Interestingly, in a recent report, higher peripheral blood γδ T cells at day +100 post ASCT in MM patients was associated with improved 2-year PFS and OS. There is a substantial interest in γδ T cells in the context of T cell-based immunotherapeutic strategies to stimulate or expand γδ T cells to improve anti-myeloma cytotoxicity. Ex vivo expansion of γδ T cells with phytohemagglutin together with IL-2 and allogeneic feeder stimulation demonstrated $V\delta1^+$ T cells cytotoxic potential against MM (U266, RPMI8226) or plasma cell leukemia (ARH77) cell lines. Another study utilizing bromohydrin pyrophosphate to expand ex vivo $\gamma9^+\delta2^-$-T-cell showed this cell subset had significant cytotoxicity against MM cell lines but also primary MM cells In a clinical trial, pan-γδ T cells expansion by pamidronate administration, combined with low dose IL-2, led to objective tumor response in MM patients with progressive disease among patients with detectable circulating γδ-T-cell prior to treatment. Upcoming studies from our laboratory with an expanded flow panel including γδ T cells should facilitate further knowledge of the function of γδ T cells expressing KIR3DL1 and their role in MM.

Besides KIRs, NKG2A inhibitory receptor can also be expressed by rare T cell subsets including γδ T cells and NK-T cells. By forming heterodimer with CD94 glycoprotein, NKG2A/CD94 potentiates NK-T cells activation upon engagement with MCH-class I molecules. Defects in the NKT cell pool have been associated with disease progression in MM. In a longitudinal analysis, while the frequency and cytokine production of NKT cells was normal in newly diagnosed MM patients, relapsed MM patients displayed significant NKT cell deficiency. In our study, low NKG2A expression by NKT-like cells was demonstrated in $MRD^{pos}$ patients compared with $MRD^{neg}$ patients.

Chemokines and chemotactic cytokines control the migratory patterns and positioning of immune cells. An extensive survey of 27 immune analytes (chemokines, cytokines and growth factors) in peripheral blood did not reveal statistically significant differences between the two groups on univariate analysis. The small cohort size may limit drawing broader conclusions, but the $MRD^{neg}$ group showed a trend towards higher concentration of serum MIP1b (also known as CCL4), and PDGF-bb and IL-1ra. The chemokine CCL4 and its receptor CCR5 are key regulators of NK cell biology. These chemokines have been implicated in NK cell egress to the bone marrow as well as bone lytic lesion in osteoporosis CCR5 is also heterogeneously expressed by γδ T cells compared with conventional CD4 T cells or CTLs. This facet will be interesting to explore in more detail in future studies by correlating the peripheral cytokine/chemokine profile with that in bone marrow to look at the relevance of interaction between myeloma cells and immune cells that takes place within the bone marrow microenvironment in $MRD^{pos}$ versus $MRD^{neg}$ responses.

This exploratory, proof-of-concept study has led us to study the immune repertoire in prospective immunotherapy based trials at our center in newly diagnosed, early relapse and advanced relapsed MM. We have initiated trials using a combination of Daratumumab/Pembrolizumab with extensive immune correlatives based on the approach used in this study. Prospective studies are also being designed to study whether the immune phenotype associated with MRD negativity involved in maintenance of remission could be used to predict which patients might successfully stop maintenance therapy and which patients might need augmentation of therapy at the loss of this phenotype. Small sample size limits generalization of our findings to clinical practice. Nonetheless our study sheds light on immune mechanisms involved in elimination of MRD and highlights the importance of incorporating immune profiling correlatives with MRD assessment in future clinical trials The foregoing is illustrative of the present invention, and is not to be construed as limiting thereof. The invention is defined by the following claims, with equivalents of the claims to be included therein.

TABLE 1

Patient Characteristics

| | Overall n = 36 | | MRD Negative n = 6 | | MRD Positive n = 30 | |
|---|---|---|---|---|---|---|
| | n | % | n | % | n | % |
| Gender | | | | | | |
| Male | 13 | 36.1 | 1 | 16.7 | 12 | 40.0 |
| Female | 23 | 63.9 | 5 | 83.3 | 18 | 60.0 |
| Age, years | | | | | | |
| Median | 60 | | 63 | | 59 | |
| Range | 24-70 | | 51-70 | | 24-70 | |
| Disease | | | | | | |
| Newly Diagnosed MM | 31 | 86.1 | 4 | 66.7 | 27 | 90.0 |
| Relapsed MM | 5 | 13.9 | 2 | 33.3 | 3 | 10.0 |
| Stage | | | | | | |
| I | 17 | 47.2 | 3 | 50.0 | 14 | 46.7 |
| II | 14 | 38.9 | 3 | 50.0 | 11 | 36.7 |
| III | 5 | 13.9 | 0 | 0.0 | 5 | 16.7 |
| Cytogenetic Risk Level | | | | | | |
| Standard | 22 | 61.1 | 4 | 66.7 | 18 | 60.0 |
| Intermediate | 2 | 5.6 | 0 | 0.0 | 2 | 6.7 |
| High | 12 | 33.3 | 2 | 33.3 | 10 | 33.3 |

TABLE 1-continued

Patient Characteristics

| | Overall n = 36 | | MRD Negative n = 6 | | MRD Positive n = 30 | |
|---|---|---|---|---|---|---|
| | n | % | n | % | n | % |
| BM Plasma Cell % (baseline) | | | | | | |
| <30% | 11 | 30.6 | 3 | 50.0 | 8 | 26.7 |
| 30-60% | 8 | 22.2 | 2 | 33.3 | 6 | 20.0 |
| >60% | 17 | 47.2 | 1 | 16.7 | 16 | 53.3 |
| Type | | | | | | |
| Light chain Kappa (IgG or IgA) | 15 | 41.7 | 3 | 50 | 12 | 40 |
| Free light chain kappa | 4 | 11.1 | 1 | 16.7 | 3 | 10 |
| Light chain Lambda (IgG or IgA) | 11 | 30.5 | 2 | 33.3 | 9 | 30 |
| Free light chain Lambda | 6 | 16.7 | 0 | 0 | 6 | 20 |

TABLE 2

Clinical response assessments post-induction therapy and post-ASCT

| | MRD Negative n = 6 | | MRD Positive n = 30 | |
|---|---|---|---|---|
| | n | % | n | % |
| Induction Therapy | | | | |
| Proteasome Inhibitor only | 1 | 16.7 | 10 | 33.3 |
| IMiD and Proteasome Inhibitor | 5 | 83.3 | 20 | 66.7 |
| To Induction | | | | |
| sCR | 0 | 0.0 | 4 | 13.3 |
| CR | 1 | 16.7 | 2 | 6.7 |
| VGPR | 4 | 66.7 | 17 | 56.7 |
| PR | 1 | 16.7 | 7 | 23.3 |
| Post-Transplant | | | | |
| sCR | 1 | 16.7 | 10 | 33.3 |
| CR | 3 | 50.0 | 6 | 20.0 |
| VGPR | 2 | 33.3 | 13 | 43.3 |
| PR | 0 | 0.0 | 1 | 3.3 |

Abbreviations:
IMiD immune modulatory drugs, sCR stringent complete response, CR complete response, VGPR very good partial response, PR partial response

TABLE 3

Antibody used flow cytometry-based MRD assay and immune phenotyping

| Marker | Channel | Clone | Supplier |
|---|---|---|---|
| MM MRD Assay | | | |
| CD38 | FITC | Multi-Epitope | ALPCO |
| CD56 | PE | C5.9 | ALPCO |
| CD45 | PerCP-Cy5.5 | HI30 | BioLegend |
| CD19 | PE-Cy7 | J3-119 | ALPCO |
| CD117 | APC | 104D2 | BD Biosciences |
| CD81 | APC-C750 | M38 | ALPCO |
| CD138 | HV450 | MI 15 | BD Biosciences |
| CD27 | BV510 | O323 | BioLegend |
| Anti-Kappa | APC | Polyclonal | Dako |
| Anti-Lambda | APC-C750 | Polyclonal | ALPCO |
| NK, NK-T, T cell phenotyping | | | |
| CD56 | FITC | B159 | BD Bioscience |
| CD158e1(KIR3DL1) | PE | DX9 | BD Bioscience |
| CD314(NKG2D) | PE-CF 594 | CD314 | BD Bioscience |
| CD159(NKG2a) | PerCP | 131411 | R&D Systems |
| CD335(NKp46) | PE-Cy7 | 9.00E+02 | BD Bioscience |
| CD158i(KIR2DS4) | Alexa 647 | 179315 | BD Bioscience |
| CD226(Tim-3) | PE | F38-2E2 | BioLegend |
| CD279(PD-1) | Alexa 647 | EH12.1 | BD Bioscience |
| CD3 | APC-C750 | UCHT-1 | APOLC |

TABLE 4

BD FACSAria II configuration

| Laser | Excitation (nm) | Detector | Dichroic Mirror | Bandpass Filter |
|---|---|---|---|---|
| Blue Argon Laser | 488 | FSC | | |
| | | SSC | | 488/10 |
| | | FITC | 502LP | 530/30 |
| | | PE | 556LP | 585/42 |
| | | PE-CF594 | 610LP | 616/23 |
| | | PerCP-Cy5.5 | 695LP | 695/40 |
| | | PE-Cy7 | 735LP | 780/60 |
| Red Helium-neon laser | 633 | Alexa647 or APC | | 660/20 |
| | | APC-C750 | 750LP | 780/60 |
| Violet Diode | 405 | BV421 or HV450 | | 450/50 |
| | | BV510 | 475LP | 525/50 |

Note:
stream-in air square flow cell type, sheath pressure 20 psi, nozzle size 100 μm. Diva version 8 software for data acquisition That which is claimed:

1. A method of treating a multiple myeloma (MM) patient, comprising:
(a) establishing a peripheral immune profile of the MM patient by the steps of:
 i) obtaining a biological sample from the MM patient;
 ii) analyzing natural killer (NK), NK-T and T cell peripheral populations and/or activation in the biological sample;
 iii) analyzing natural killer group (NKG) 2D (NKG2D) expression in NK and NK-T cells in the biological sample;
 iv) analyzing killer cell immunoglobulin-like receptor 3DL1 (KIR3DL1) expression in NK and T cells in the biological sample;
 v) analyzing NKG2A expression in NK, NK-T and T cells in the biological sample;
 vi) analyzing T-cell immunoglobulin and mucin-domain containing-3 (Tim3) expression in NK-T cells in the biological sample; and
 vii) quantifying interleukin (IL)-12p70 (IL-12p70) and IL-17 pro-inflammatory cytokines and/or quantifying fibroblast growth factor (FGF), platelet-derived growth factor (PDGF) and vascular endothelial growth factor (VEGF) pro-angiogenic growth factors in the biological sample;
b) comparing the peripheral immune profile of (a) to a pre-determined threshold, wherein the pre-determined threshold is established from peripheral immune profiles from a known population of minimal residue disease positive (MRD$^{pos}$) and minimal residue disease negative (MRD$^{neg}$) patients, wherein if the peripheral immune profile of (a) exceeds the pre-determined threshold, the MM patient is positive for MRD and if the peripheral immune profile of (a) is equal to or does not exceed the pre-determined threshold, the MM patient is negative for MRD; and c) treating the patient having a peripheral immune profile that exceeds the pre-determined threshold, wherein the treatment is selected from steroids, stem cell transplantation, autologous stem cell transplantation (ASCT), induction therapy, thalidomide, lenalidomide, pomalidomide, proteasome inhibitor treatment, bortezomib-dexamethasone (VD), bortezomib-cyclophosphamide-dexamethasone with daratumumab (CyBorD-Dara), bortezomib-cyclophosphamide-dexamethasone without daratumumab (CyBorD), carfilzomib-cytoxan-dexamethasone (Car-Cy-Dex), bortezomib-melphalan-prednisone with daratumumab (VMP-Dara), bortezomib-melphalan-prednisone without daratumumab (VMP), bortezomib-dexamethasone-cisplatin-Adriamycin-cyclophosphamide-etoposide (VD-PACE), combination Daratumumab/Pembrolizumab, and any combination thereof.

2. The method of claim 1, wherein the MM patient is a newly diagnosed and untreated patient, a newly diagnosed patient undergoing treatment, or a relapsed patient undergoing salvage treatments or salvage transplants.

3. The method of claim 1, wherein the patient has received an autologous stem cell transplantation (ASCT) prior to steps a)-c).

4. The method of claim 1, wherein the pre-determined threshold is established from peripheral immune profiles of a known population of MRD$^{pos}$ and MRD$^{neg}$ patients by the steps of:
(a) establishing a peripheral immune profile of each patient in a control population of known MM patients in remission, by the steps of:
  i) obtaining a biological sample from each MM patient;
  ii) analyzing natural killer (NK), NK-T and T cell peripheral populations and/or activation in each biological sample;
  iii) analyzing natural killer group (NKG) 2D (NKG2D) expression in NK and NK-T cells in each biological sample;
  iv) analyzing killer cell immunoglobulin-like receptor 3DL1 (KIR3DL1) expression in NK and T cells in each biological sample;
  v) analyzing NKG2A expression in NK, NK-T and T cells in each biological sample;
  vi) analyzing T-cell immunoglobulin and mucin-domain containing-3 (Tim3) expression in NK-T cells in each biological sample; and
  vii) quantifying interleukin (IL)-12p70 (IL-12p70) and IL-17 pro-inflammatory cytokines and/or quantifying fibroblast growth factor (FGF), platelet-derived growth factor (PDGF) and vascular endothelial growth factor (VEGF) pro-angiogenic growth factors in each biological sample;
b) measuring abnormal/clonal plasma cell count in each biological sample to determine MRD status of each known MM patient, wherein an abnormal/clonal plasma cell count of less than or equal to $1.5\times10^{-5}$ identifies MRD$^{neg}$ status, and an abnormal/clonal plasma cell count of greater than $1.5\times10^{-5}$ identifies MRD$^{pos}$ status;
c) associating the peripheral immune profile and MRD status of each biological sample; and
d) determining a threshold distinguishing MRD$^{pos}$ and MRD$^{neg}$ peripheral immune profiles of the known population of MM patients.

5. A method of treating a multiple myeloma (MM) patient at increased risk of progression to active MM, comprising:
(a) establishing a peripheral immune profile of the MM patient by the steps of:
  i) obtaining a biological sample from the MM patient;
  ii) analyzing natural killer (NK), NK-T and T cell peripheral populations and/or activation in the biological sample;
  iii) analyzing natural killer group (NKG) 2D (NKG2D) expression in NK and NK-T cells in the biological sample;
  iv) analyzing killer cell immunoglobulin-like receptor 3DL1 (KIR3DL1) expression in NK and T cells in the biological sample;
  v) analyzing NKG2A expression in NK, NK-T and T cells in the biological sample;
  vi) analyzing T-cell immunoglobulin and mucin-domain containing-3 (Tim3) expression in NK-T cells in the biological sample; and
  vii) quantifying interleukin (IL)-12p70 (IL-12p70) and IL-17 pro-inflammatory cytokines and/or quantifying fibroblast growth factor (FGF), platelet-derived growth factor (PDGF) and vascular endothelial growth factor (VEGF) pro-angiogenic growth factors in the biological sample;
b) comparing the peripheral immune profile of (a) to a pre-determined threshold, wherein the pre-determined threshold is established from peripheral immune profiles of a known population of MRD$^{pos}$ and MRD$^{neg}$ patients, wherein if the peripheral immune profile of (a) exceeds the pre-determined threshold, the MM patient is positive for MRD and if the peripheral immune profile of (a) is equal to or does not exceed the pre-determined threshold, the MM patient is negative for MRD;
c) identifying the patient as having an increased risk of progression to active MM because the patient has a peripheral immune profile that exceeds the pre-determined threshold; and
d) treating the patient identified as having an increased risk of progression to active MM to decrease the patient's risk of progression to active MM.

6. The method of claim 5, wherein the patient has received an autologous stem cell transplantation (ASCT) prior to steps a)-d).

7. The method of claim 5, wherein the pre-determined threshold is established from peripheral immune profiles of a known population of MRD$^{pos}$ and MRD$^{neg}$ patients by the steps of:
(a) establishing a peripheral immune profile of each patient in a control population of known MM patients in remission, by the steps of:
  i) obtaining a biological sample from each MM patient;
  ii) analyzing natural killer (NK), NK-T and T cell peripheral populations and/or activation in each biological sample;
  iii) analyzing natural killer group (NKG) 2D (NKG2D) expression in NK and NK-T cells in each biological sample;
  iv) analyzing killer cell immunoglobulin-like receptor 3DL1 (KIR3DL1) expression in NK and T cells in each biological sample;
  v) analyzing NKG2A expression in NK, NK-T and T cells in each biological sample;
  vi) analyzing T-cell immunoglobulin and mucin-domain containing-3 (Tim3) expression in NK-T cells in each biological sample; and vii) quantifying interleukin (IL)-12p70 (IL-12p70) and IL-17 pro-inflammatory cytokines and/or quantifying fibroblast growth factor (FGF), platelet-derived growth factor (PDGF) and vascular endothelial growth factor (VEGF) pro-angiogenic growth factors in each biological sample;

b) measuring abnormal/clonal plasma cell count in each biological sample to determine MRD status of each known MM patient, wherein an abnormal/clonal plasma cell count of less than or equal to $1.5 \times 10^{-5}$ identifies $MRD^{neg}$ status, and an abnormal/clonal plasma cell count of greater than $1.5 \times 10^{-5}$ identifies $MRD^{pos}$ status;

c) associating the peripheral immune profile and MRD status of each biological sample; and d) determining a threshold distinguishing $MRD^{pos}$ and $MRD^{neg}$ peripheral immune profiles of the known population of MM patients.

\* \* \* \* \*

UNITED STATES PATENT AND TRADEMARK OFFICE
CERTIFICATE OF CORRECTION

PATENT NO. : 10,656,144 B2
APPLICATION NO. : 15/829611
DATED : May 19, 2020
INVENTOR(S) : Usmani et al.

Page 1 of 1

It is certified that error appears in the above-identified patent and that said Letters Patent is hereby corrected as shown below:

In the Specification

Column 3, Line 51: Please correct "$CD56^{high}, CD3^+ CD56^-$)" to read -- $CD56^{high}, CD3^+ CD56^+ CD3^+ CD56^-$) --

Column 6, Line 67: Please correct "ica" to read -- κ/λ --

Column 13, Line 26: Please correct "($CD56^- {}^{CD}3^+$)" to read -- ($CD56^- CD3^+$) --

In the Claims

Column 19, Line 50, Claim 4: Please correct "(IL-1'2p70)" to read -- (IL-12p70) --

Signed and Sealed this
Twentieth Day of October, 2020

Andrei Iancu
*Director of the United States Patent and Trademark Office*